(12) United States Patent
Smith et al.

(10) Patent No.: US 11,833,393 B2
(45) Date of Patent: Dec. 5, 2023

(54) SYSTEM AND METHOD FOR USING AN EXERCISE MACHINE TO IMPROVE COMPLETION OF AN EXERCISE

(71) Applicant: Rehab2Fit Technologies Inc., Longmont, CO (US)

(72) Inventors: Colin James Smith, Boulder, CO (US); Michael Bissonnette, Denver, CO (US); Steven Mason, Las Vegas, NV (US); James D. Steidl, San Diego, CA (US)

(73) Assignee: REHAB2FIT TECHNOLOGIES, INC., Longmont, CO (US)

( * ) Notice: Subject to any disclaimer, the term of this patent is extended or adjusted under 35 U.S.C. 154(b) by 66 days.

(21) Appl. No.: 16/874,052

(22) Filed: May 14, 2020

(65) Prior Publication Data

US 2020/0360764 A1    Nov. 19, 2020

Related U.S. Application Data

(60) Provisional application No. 62/848,313, filed on May 15, 2019.

(51) Int. Cl.
*A63B 24/00* (2006.01)
*A63B 21/00* (2006.01)
(Continued)

(52) U.S. Cl.
CPC ...... *A63B 24/0062* (2013.01); *A63B 21/4034* (2015.10); *A63B 21/4035* (2015.10);
(Continued)

(58) Field of Classification Search
None
See application file for complete search history.

(56) References Cited

U.S. PATENT DOCUMENTS

| 3,017,180 A | 1/1962 | Aronsohn |
| 3,213,852 A | 10/1965 | Zent |

(Continued)

FOREIGN PATENT DOCUMENTS

| CN | 2885238 Y | 4/2007 |
| CN | 103473631 A | 12/2013 |

(Continued)

OTHER PUBLICATIONS

U.S. Appl. No. 16/812,462, filed Mar. 9, 2020, and titled "System, Method and Apparatus for Adjustable Pedal Crank", by Peter Arn, et al.

(Continued)

*Primary Examiner* — Shila Jalalzadeh Abyaneh
(74) *Attorney, Agent, or Firm* — Dickinson Wright PLLC; Stephen A. Mason; Jonathan H. Harder

(57) ABSTRACT

A system and method for improving completion of an exercise is disclosed herein. In one embodiment, a method of a control system to improve compliance with an exercise plan for an exercise machine includes receiving one or more load measurements from one or more load cells of the exercise machine. The method also includes comparing the one or more load measurements to one or more target thresholds, and determining whether the one or more load measurements exceed the one or more target thresholds. Responsive to determining that the one or more load measurements exceed the one or more target thresholds, the method also includes causing a user interface to present an indication that the one or more target thresholds have been exceeded and an exercise is complete, wherein the exercise is included in the exercise plan.

15 Claims, 28 Drawing Sheets

(51) Int. Cl.
*A63B 71/06* (2006.01)
*A63B 22/20* (2006.01)
*A63B 22/06* (2006.01)
*A63B 22/00* (2006.01)

(52) U.S. Cl.
CPC ...... *A63B 22/0005* (2015.10); *A63B 22/0605* (2013.01); *A63B 22/203* (2013.01); *A63B 24/0075* (2013.01); *A63B 71/0622* (2013.01); *A63B 2022/0094* (2013.01); *A63B 2024/0068* (2013.01); *A63B 2071/0627* (2013.01); *A63B 2071/0652* (2013.01); *A63B 2208/0233* (2013.01); *A63B 2220/50* (2013.01)

(56) References Cited

U.S. PATENT DOCUMENTS

| | | |
|---|---|---|
| 4,222,376 A | 9/1980 | Martin |
| 4,538,804 A | 9/1985 | Zibell |
| 4,860,763 A | 8/1989 | Schminke |
| 5,139,255 A | 8/1992 | Sollami |
| 5,184,991 A | 2/1993 | Brangi |
| 5,230,672 A * | 7/1993 | Brown ................ A63B 21/154 482/4 |
| 5,857,943 A | 1/1999 | Murray |
| 5,980,431 A | 11/1999 | Miller |
| 6,007,459 A | 12/1999 | Burgess |
| 6,613,000 B1 | 9/2003 | Reinkensmeyer et al. |
| 6,960,155 B2 | 11/2005 | Chien |
| 7,063,643 B2 | 6/2006 | Arai |
| 7,510,512 B1 | 3/2009 | Taggett |
| 7,628,730 B1 | 12/2009 | Watterson et al. |
| 7,837,472 B1 | 11/2010 | Elsmore et al. |
| 7,969,315 B1 | 6/2011 | Ross et al. |
| 8,038,578 B2 | 10/2011 | Olrik et al. |
| 8,298,123 B2 | 10/2012 | Hickman |
| 8,371,990 B2 | 2/2013 | Shea |
| 8,409,060 B2 | 4/2013 | Hsu |
| 8,444,534 B2 | 5/2013 | Mckee |
| 8,818,496 B2 | 8/2014 | Dziubinski et al. |
| 8,893,287 B2 | 11/2014 | Gjonej et al. |
| 9,272,186 B2 | 3/2016 | Reich |
| 9,486,382 B1 | 11/2016 | Boss |
| 9,640,057 B1 | 5/2017 | Ross |
| 9,977,587 B2 | 5/2018 | Mountain |
| 9,987,188 B1 | 6/2018 | Diao |
| 9,993,181 B2 | 6/2018 | Ross |
| 10,004,946 B2 | 6/2018 | Ross |
| D826,349 S | 8/2018 | Oblamski |
| 10,089,443 B2 | 10/2018 | Miller et al. |
| 10,130,311 B1 | 11/2018 | De Sapio et al. |
| 10,173,094 B2 | 1/2019 | Somberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,278,883 B2 | 5/2019 | Walsh |
| 10,380,866 B1 | 8/2019 | Ross et al. |
| D866,957 S | 11/2019 | Ross et al. |
| 10,475,323 B1 | 11/2019 | Ross |
| 10,532,000 B1 | 1/2020 | De Sapio |
| 10,532,785 B2 | 1/2020 | Stillman |
| 10,646,746 B1 | 5/2020 | Gomberg et al. |
| D899,605 S | 10/2020 | Ross et al. |
| 10,867,695 B2 | 12/2020 | Neagle |
| 10,946,239 B2 | 3/2021 | Berry |
| 11,093,904 B2 | 8/2021 | Humble |
| D939,096 S | 12/2021 | Lee |
| D940,891 S | 1/2022 | Lee |
| 11,386,176 B2 | 7/2022 | Galitsky |
| 11,433,276 B2 | 9/2022 | Bissonnette |
| 11,458,354 B2 | 10/2022 | Bissonnette et al. |
| 11,458,363 B2 | 10/2022 | Powers et al. |
| 11,636,944 B2 | 4/2023 | Hanrahan et al. |
| 2002/0143279 A1 | 10/2002 | Porter et al. |
| 2003/0036683 A1 | 2/2003 | Kehr et al. |
| 2003/0093012 A1 * | 5/2003 | Smyser ................ G16H 20/30 600/595 |
| 2004/0204959 A1 | 10/2004 | Moreano et al. |
| 2004/0259693 A1 | 12/2004 | Chien |
| 2005/0101463 A1 | 5/2005 | Chen |
| 2006/0079817 A1 | 4/2006 | Dewald |
| 2006/0135325 A1 | 6/2006 | Holness |
| 2006/0229164 A1 | 10/2006 | Einav |
| 2006/0252607 A1 | 11/2006 | Holloway |
| 2006/0258520 A1 | 11/2006 | Bowser |
| 2007/0099766 A1 | 5/2007 | Pyles |
| 2007/0118389 A1 | 5/2007 | Shipon |
| 2007/0149364 A1 | 6/2007 | Blau |
| 2007/0243980 A1 | 10/2007 | Bowser |
| 2007/0271065 A1 * | 11/2007 | Gupta ................ G11B 27/105 702/158 |
| 2008/0119333 A1 | 5/2008 | Bowser |
| 2008/0139975 A1 | 6/2008 | Einav |
| 2009/0023556 A1 * | 1/2009 | Daly ................ A63B 24/0062 482/9 |
| 2009/0221407 A1 | 9/2009 | Hauk |
| 2009/0239714 A1 | 9/2009 | Sellers |
| 2010/0022354 A1 | 1/2010 | Fisher |
| 2010/0029445 A1 | 2/2010 | Lee |
| 2010/0035726 A1 | 2/2010 | Fisher |
| 2010/0035729 A1 | 2/2010 | Pandozy |
| 2010/0152629 A1 | 6/2010 | Haas |
| 2010/0234184 A1 * | 9/2010 | Le Page ................ A61B 5/1118 482/8 |
| 2010/0261585 A1 | 10/2010 | Hauk |
| 2010/0298102 A1 | 11/2010 | Bosecker et al. |
| 2010/0331144 A1 | 12/2010 | Rindfleisch |
| 2011/0143898 A1 * | 6/2011 | Trees ................ A61G 7/005 482/142 |
| 2011/0165995 A1 | 7/2011 | Paulus |
| 2011/0172058 A1 | 7/2011 | Deaconu |
| 2011/0256983 A1 | 10/2011 | Malack |
| 2012/0040799 A1 * | 2/2012 | Jaquish ................ A63B 23/0355 482/9 |
| 2012/0232438 A1 | 9/2012 | Cataldi et al. |
| 2013/0029809 A1 | 1/2013 | Spevak |
| 2013/0102440 A1 * | 4/2013 | Hutchins ................ A63B 24/00 482/8 |
| 2013/0211281 A1 | 8/2013 | Ross et al. |
| 2013/0282157 A1 * | 10/2013 | Shin ................ G16H 20/30 700/91 |
| 2013/0345604 A1 | 12/2013 | Nakamura |
| 2014/0113768 A1 | 4/2014 | Lin et al. |
| 2014/0113776 A1 | 4/2014 | Jaguan |
| 2014/0195103 A1 | 7/2014 | Nassef |
| 2014/0243160 A1 | 8/2014 | Lim |
| 2014/0257535 A1 * | 9/2014 | Morris ................ A61B 5/1123 700/91 |
| 2014/0274564 A1 | 9/2014 | Greenbaum |
| 2015/0025816 A1 | 1/2015 | Ross |
| 2015/0065303 A1 | 3/2015 | Born |
| 2015/0065305 A1 | 3/2015 | Dalton |
| 2015/0094192 A1 | 4/2015 | Skwortsow et al. |
| 2015/0165263 A1 | 6/2015 | Golen |
| 2015/0257679 A1 | 9/2015 | Ross |
| 2015/0351664 A1 | 12/2015 | Ross |
| 2015/0351665 A1 | 12/2015 | Ross |
| 2015/0360069 A1 | 12/2015 | Marti et al. |
| 2016/0136483 A1 | 5/2016 | Reich |
| 2016/0184634 A1 | 6/2016 | Yanev |
| 2016/0220866 A1 * | 8/2016 | Feichtinger ............ G16H 20/30 |
| 2016/0220867 A1 | 8/2016 | Flaherty |
| 2016/0271438 A1 | 9/2016 | Weisz |
| 2017/0003311 A1 | 1/2017 | Lay |
| 2017/0021827 A1 | 1/2017 | Seagraves |
| 2017/0036055 A1 | 2/2017 | Fleming |
| 2017/0065849 A1 | 3/2017 | Konishi |
| 2017/0100628 A1 | 4/2017 | Wilt |
| 2017/0132947 A1 | 5/2017 | Maeda et al. |
| 2017/0148297 A1 | 5/2017 | Ross |
| 2017/0216670 A1 * | 8/2017 | Kuroda ................ G09B 19/003 |

(56) References Cited

U.S. PATENT DOCUMENTS

| | | | |
|---|---|---|---|
| 2017/0304680 A1* | 10/2017 | Schmidt | A63B 23/03525 |
| 2017/0361165 A1 | 12/2017 | Miller | |
| 2018/0036593 A1 | 2/2018 | Ridgel et al. | |
| 2018/0064991 A1 | 3/2018 | Yanev | |
| 2018/0096111 A1 | 4/2018 | Wells et al. | |
| 2018/0177612 A1 | 6/2018 | Trabish et al. | |
| 2018/0177664 A1* | 6/2018 | Choi | A63B 23/10 |
| 2018/0178059 A1 | 6/2018 | Hyungsoon et al. | |
| 2018/0236307 A1* | 8/2018 | Hyde | G09B 19/0038 |
| 2018/0264312 A1 | 9/2018 | Pompile et al. | |
| 2018/0326243 A1 | 11/2018 | Badi et al. | |
| 2019/0060699 A1 | 2/2019 | Frederick et al. | |
| 2019/0080802 A1 | 3/2019 | Ziobro et al. | |
| 2019/0118038 A1 | 4/2019 | Tana et al. | |
| 2019/0183715 A1 | 6/2019 | Kapure et al. | |
| 2019/0192912 A1 | 6/2019 | Radow | |
| 2019/0247718 A1 | 8/2019 | Blevins | |
| 2019/0262655 A1 | 8/2019 | Lentine | |
| 2019/0275368 A1 | 9/2019 | Maroldi | |
| 2019/0290965 A1 | 9/2019 | Oren | |
| 2020/0006639 A1 | 1/2020 | Wu et al. | |
| 2020/0085300 A1 | 3/2020 | Kwatra et al. | |
| 2020/0114207 A1 | 4/2020 | Weldemariam | |
| 2020/0410893 A1* | 12/2020 | Ridington | A63B 71/0619 |
| 2021/0005319 A1 | 1/2021 | Otsuki et al. | |
| 2021/0035674 A1 | 2/2021 | Volosin et al. | |
| 2021/0113877 A1 | 4/2021 | Chin | |
| 2021/0245003 A1 | 8/2021 | Turner | |
| 2021/0268335 A1 | 9/2021 | Mizukura | |
| 2021/0361514 A1 | 11/2021 | Choi et al. | |
| 2021/0398668 A1 | 12/2021 | Chock et al. | |
| 2022/0001232 A1 | 1/2022 | DeForest | |
| 2022/0072362 A1 | 3/2022 | Hopson | |
| 2022/0118218 A1 | 4/2022 | Bense et al. | |
| 2022/0133576 A1 | 5/2022 | Choi et al. | |
| 2022/0238222 A1 | 7/2022 | Neuberg | |
| 2022/0266094 A1 | 8/2022 | Mason et al. | |
| 2022/0273985 A1 | 9/2022 | Jeong et al. | |
| 2022/0304881 A1 | 9/2022 | Choi et al. | |
| 2022/0304882 A1 | 9/2022 | Choi | |
| 2022/0305328 A1 | 9/2022 | Choi et al. | |
| 2022/0327714 A1 | 10/2022 | Cook et al. | |
| 2022/0327807 A1 | 10/2022 | Cook et al. | |
| 2022/0339052 A1 | 10/2022 | Kim | |
| 2022/0395232 A1 | 12/2022 | Locke | |
| 2022/0401783 A1 | 12/2022 | Choi | |
| 2022/0415469 A1 | 12/2022 | Mason | |
| 2022/0415471 A1 | 12/2022 | Mason | |
| 2023/0001268 A1 | 1/2023 | Bissonnette et al. | |
| 2023/0013530 A1 | 1/2023 | Mason | |
| 2023/0014598 A1 | 1/2023 | Mason et al. | |
| 2023/0048040 A1 | 2/2023 | Hacking et al. | |
| 2023/0051751 A1 | 2/2023 | Hacking et al. | |
| 2023/0058605 A1 | 2/2023 | Mason | |
| 2023/0060039 A1 | 2/2023 | Mason | |
| 2023/0072368 A1 | 3/2023 | Mason et al. | |
| 2023/0078793 A1 | 3/2023 | Mason | |
| 2023/0119461 A1 | 4/2023 | Mason | |

FOREIGN PATENT DOCUMENTS

| | | |
|---|---|---|
| CN | 103136447 B | 8/2016 |
| CN | 110808092 A | 2/2020 |
| CN | 111790111 A | 10/2020 |
| CN | 114203274 A | 3/2022 |
| CN | 114632302 A | 6/2022 |
| CN | 114898832 A | 8/2022 |
| CN | 110270062 B | 10/2022 |
| EP | 0383137 A2 | 8/1990 |
| EP | 1391179 A1 | 2/2004 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3671700 A1 | 6/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4112033 A1 | 1/2023 |
| GB | 2512431 A | 10/2014 |
| JP | 2005227928 A | 8/2005 |
| JP | 2019028647 A | 2/2019 |
| JP | 2022521378 A | 4/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20140128630 A | 11/2014 |
| KR | 20150078191 A | 7/2015 |
| KR | 20190029175 A | 3/2019 |
| KR | 101969392 B1 | 8/2019 |
| KR | 102055279 B1 | 12/2019 |
| KR | 20200029180 A | 3/2020 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102352602 B1 | 1/2022 |
| KR | 102352603 B1 | 1/2022 |
| KR | 102352604 B1 | 1/2022 |
| KR | 102387577 B1 | 4/2022 |
| KR | 102421437 B1 | 7/2022 |
| KR | 20220102207 A | 7/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| TW | 200910231 A | 3/2009 |
| TW | 201531278 A | 8/2015 |
| WO | 02062211 A2 | 8/2002 |
| WO | 2009008968 A1 | 1/2009 |
| WO | 2012128801 A1 | 9/2012 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015112945 A1 | 7/2015 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2019075185 A1 | 4/2019 |
| WO | 2020229705 A1 | 11/2020 |
| WO | 2021022003 A1 | 2/2021 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |

OTHER PUBLICATIONS

U.S. Appl. No. 16/813,158, filed Mar. 9, 2020, and titled "System, Method and Apparatus for a Rehabilitation Machine With a Simulated Flywheel", by S. Adam Hacking, et al.

U.S. Appl. No. 16/813,303, filed Mar. 9, 2020, and titled "Control System for a Rehabilitation and Exercise Electromechanical Device", by S. Adam Hacking, et al.

(56) References Cited

OTHER PUBLICATIONS

U.S. Appl. No. 16/813,224, filed Mar. 9, 2020, and titled "System, Method and Apparatus for Electrically Actuated Pedal for an Exercise or Rehabilitation Machine", by S. Adam Hacking, et al.

Jeong et al., "Computer-assisted upper extremity training using interactive biking exercise (iBikE) platform," Sep. 2012, pp. 1-5, 34th Annual International Conference of the IEEE EMBS.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age significantly-affects health-longevity/, Mayo Clinic News Network, May 20, 2021, retrieved: Jan. 23, 2023, p. 1-4.

\* cited by examiner

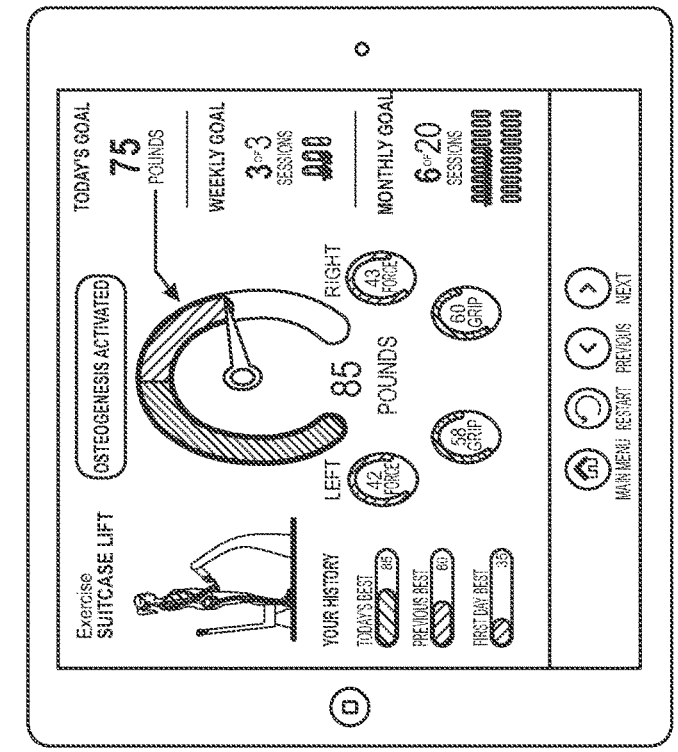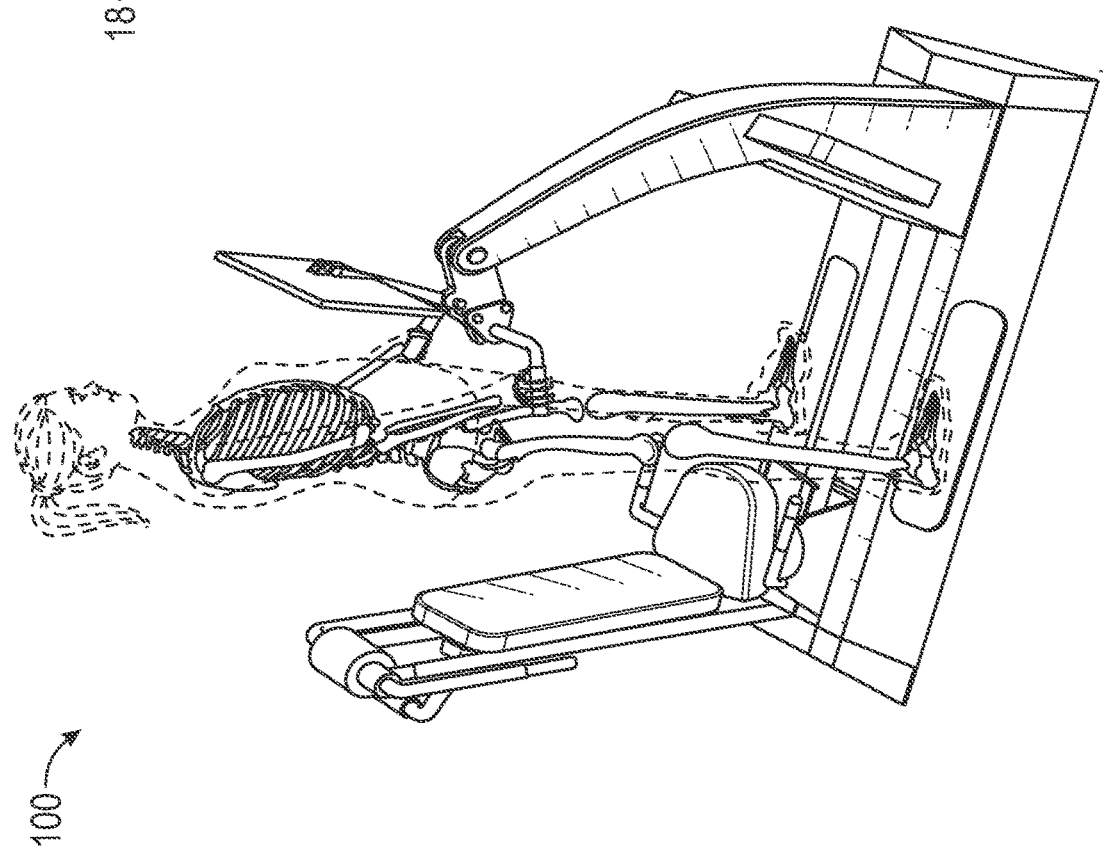
FIG. 11

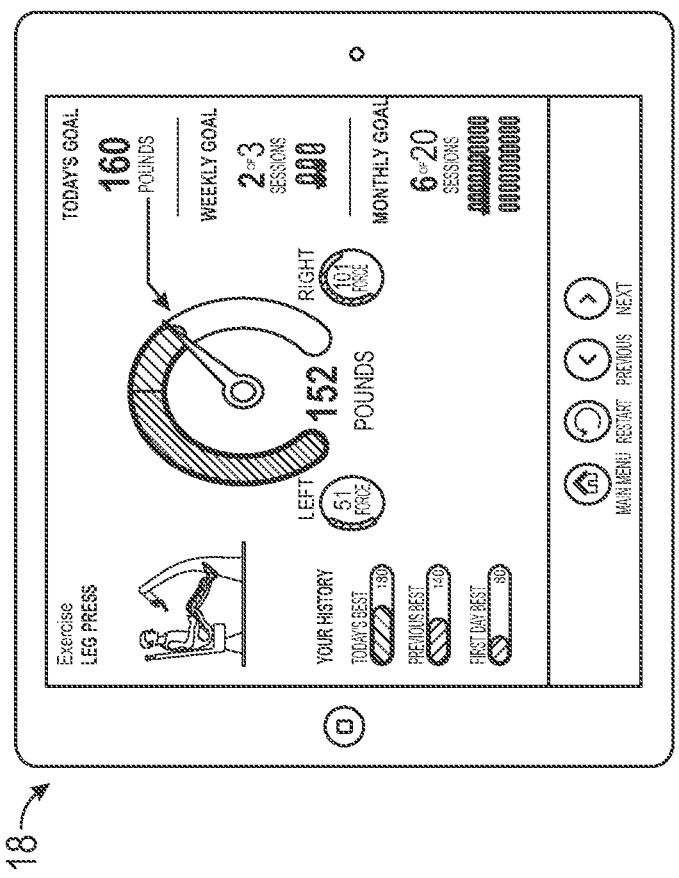
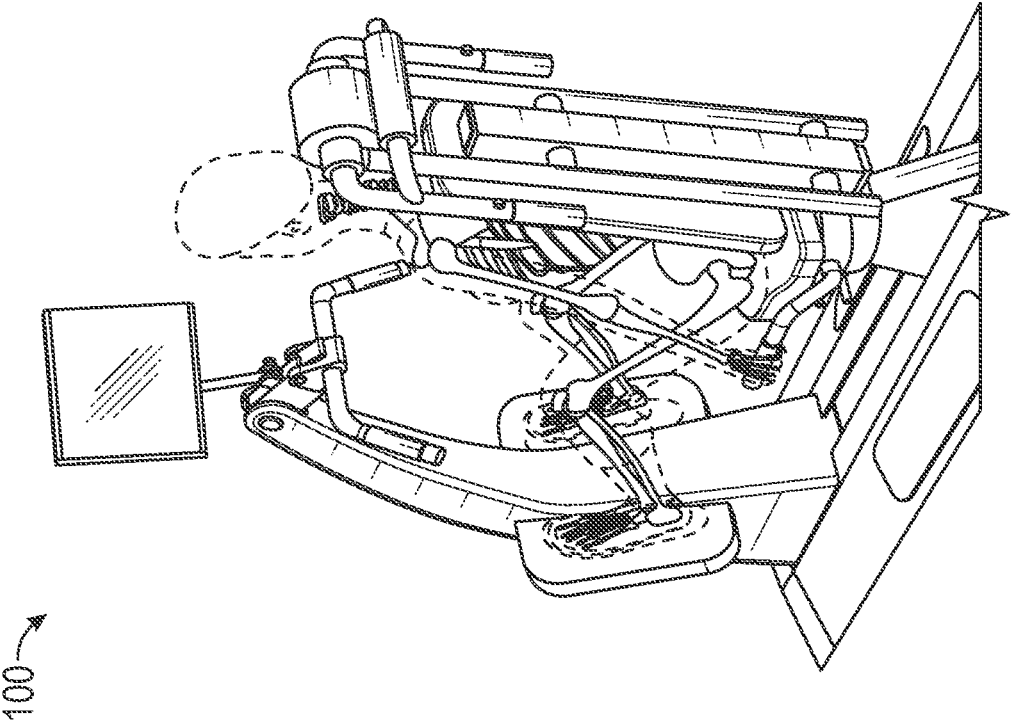
FIG. 13

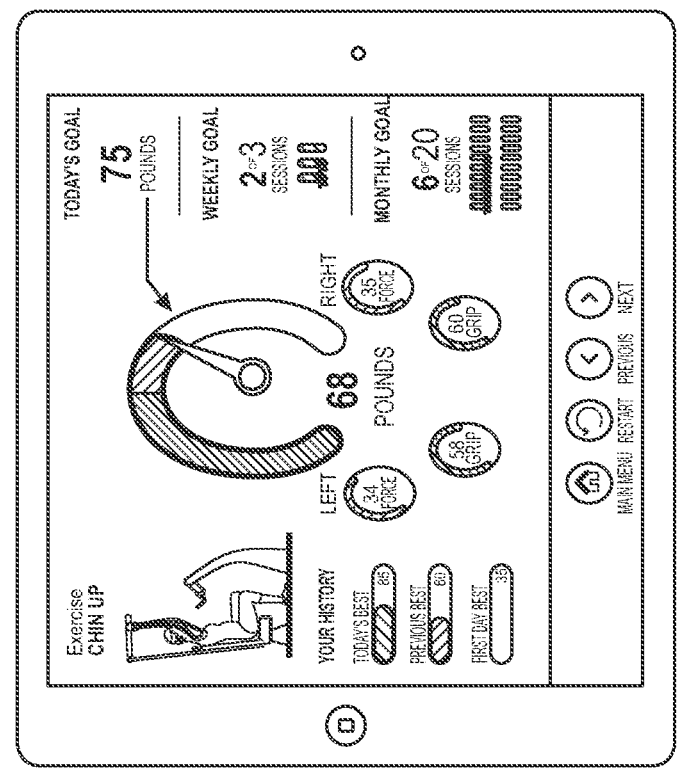
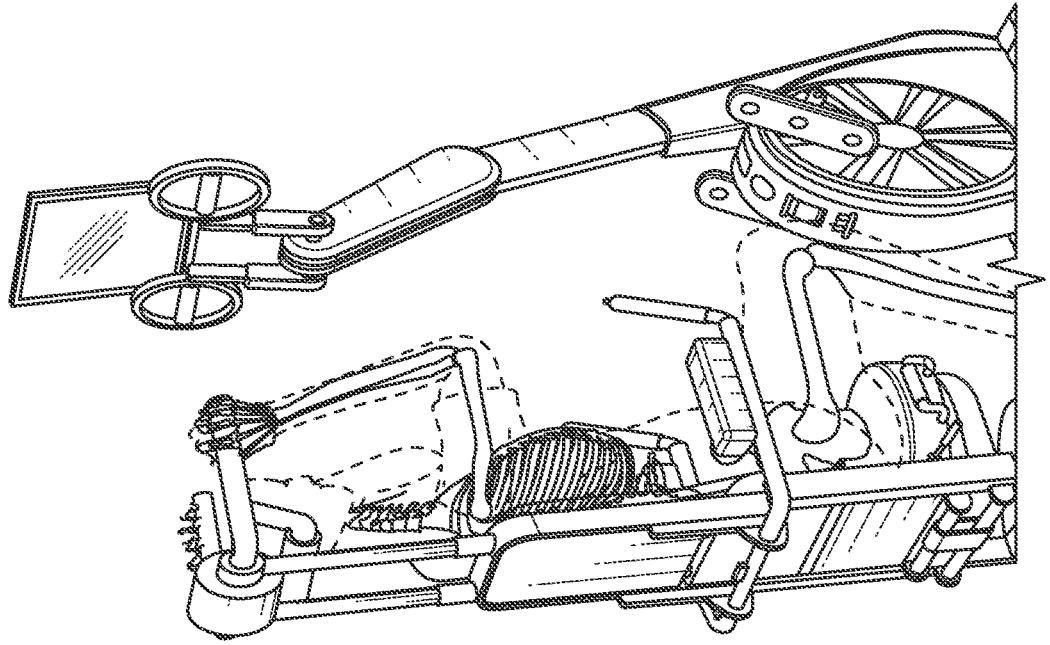
FIG. 15

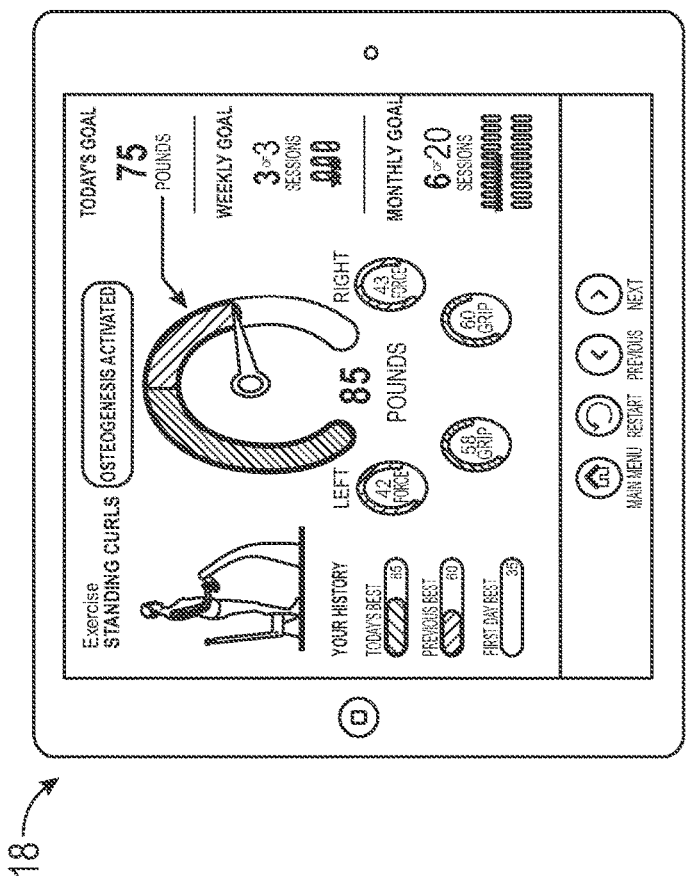
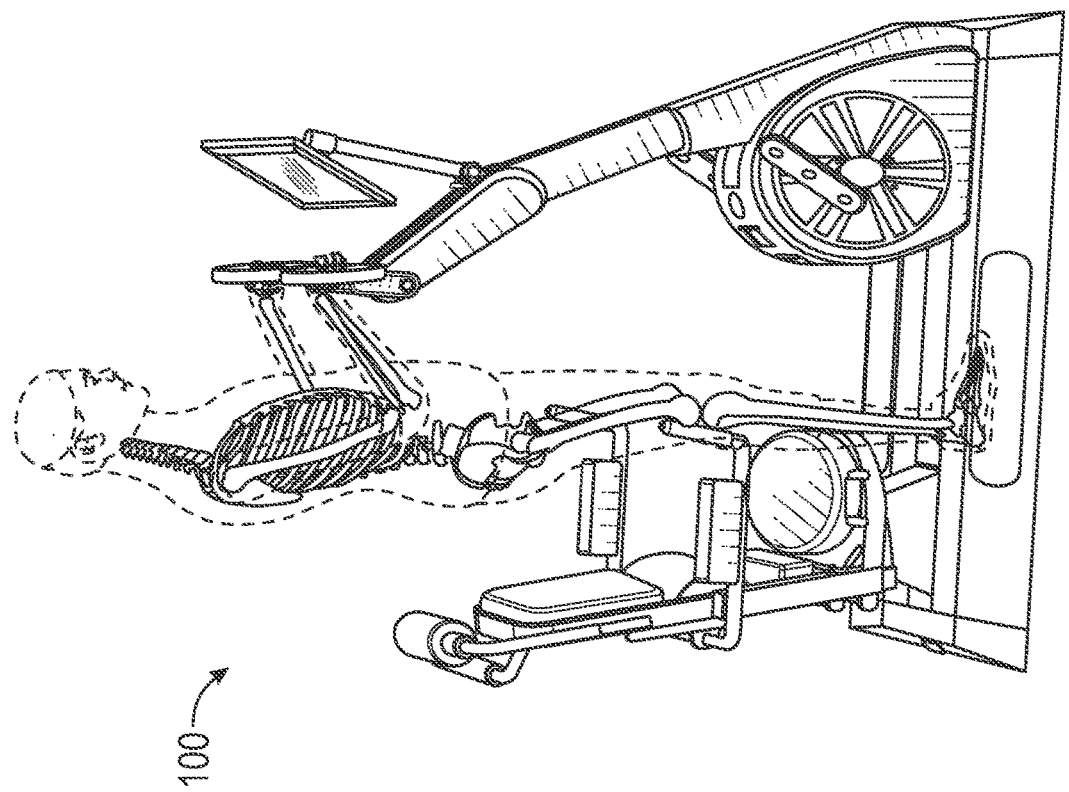
FIG. 16

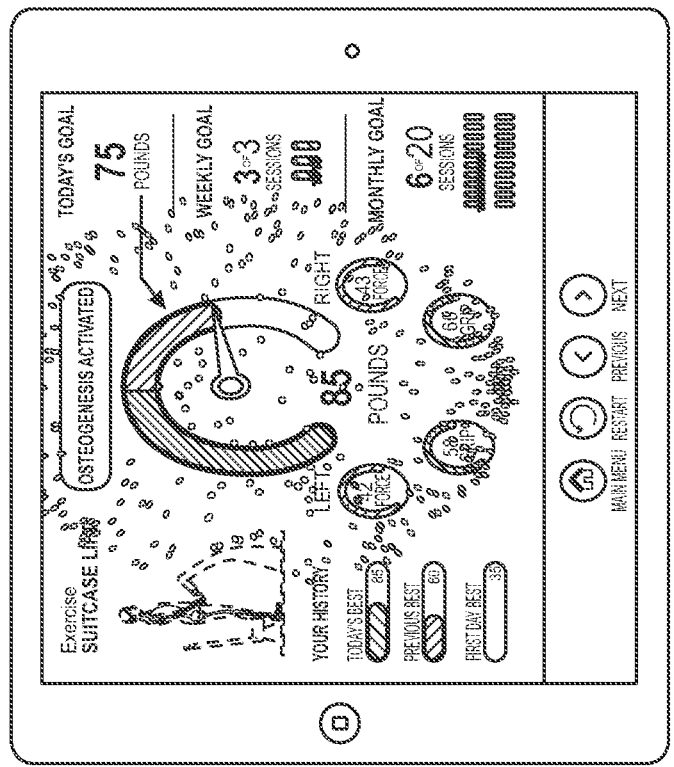
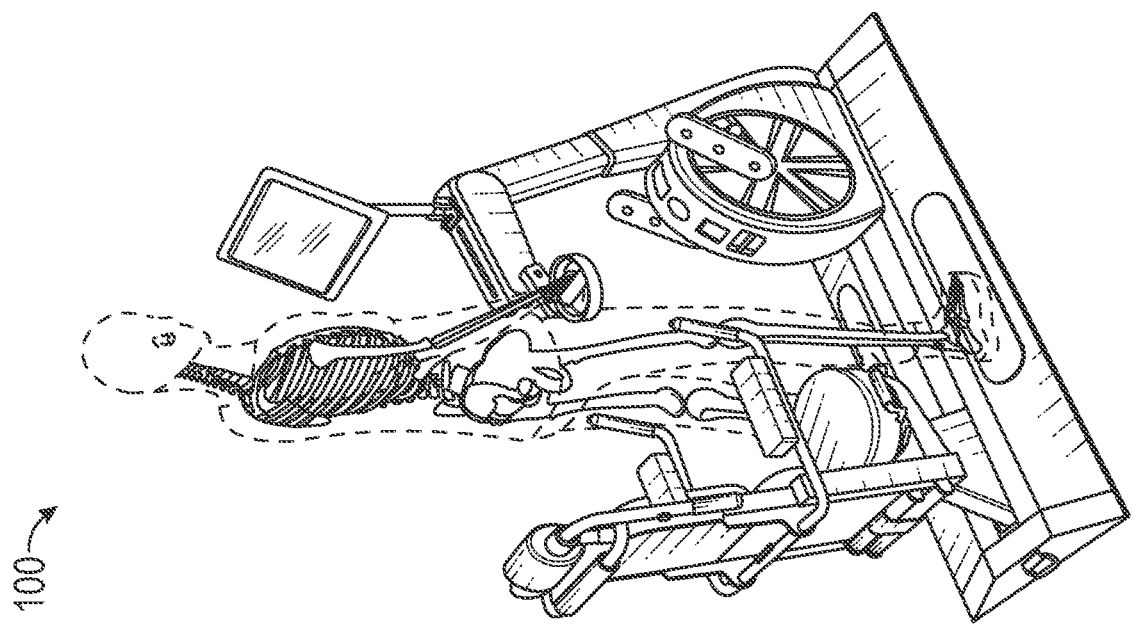
FIG. 18

```
                                                              2000
```

```
┌─────────────────────────────────────────────────────────────┐
│  Receiving one or more load measurements from one or more   │
│             load cells of the exercise machine              │
│                            2002                             │
└─────────────────────────────────────────────────────────────┘
                              ↓
┌─────────────────────────────────────────────────────────────┐
│  Comparing the one or more load measurements to one or      │
│                 more target thresholds                      │
│                            2004                             │
└─────────────────────────────────────────────────────────────┘
                              ↓
┌─────────────────────────────────────────────────────────────┐
│  Determine whether the one or more load measurements        │
│             exceed the one or more target thresholds        │
│                            2006                             │
└─────────────────────────────────────────────────────────────┘
                              ↓
┌─────────────────────────────────────────────────────────────┐
│  Responsive to determining that the one or more load        │
│  measurements satisfy the one or more target thresholds,    │
│  causing a user interface to present an indication that     │
│  the one or more target thresholds have been satisfied      │
│  and an exercise is complete, wherein the exercise is       │
│               included in the exercise plan                 │
│                            2008                             │
└─────────────────────────────────────────────────────────────┘
```

Receive, from a processing device of a control system, one or more load measurements obtained from one or more load cells included in the exercise machine
2102

Present one or more visual representations for the one or more load measurements in a user interface on a display screen
2104

Receive an indication that an exercise in the exercise plan is complete based on the one or more load measurements having satisfied one or more target thresholds
2106

Present, with the one or more visual representations, the indication in the user interface that the exercise is complete
2108

FIG. 21

SYSTEM AND METHOD FOR USING AN EXERCISE MACHINE TO IMPROVE COMPLETION OF AN EXERCISE

CROSS-REFERENCE TO RELATED APPLICATIONS

This application claims priority to and the benefit of U.S. Provisional Application Patent Ser. No. 62/848,313, filed May 15, 2019, the entire disclosure of which is hereby incorporated by reference in its entirety for all purposes.

TECHNICAL FIELD

This disclosure relates to exercise machines. More specifically, this disclosure relates to a system and method for improving completion of an exercise using an exercise machine.

BACKGROUND

Osteogenic isometric exercise and/or rehabilitation and/or strength training equipment is used to facilitate isometric exercises. A user may perform an exercise (e.g., bench press, pull down, arm curl, etc.) using the osteogenic isometric exercise and/or rehabilitation and/or strength training equipment to improve osteogenesis, bone growth, bone density, muscular hypertrophy, or some combination thereof. The isometric exercise and/or rehabilitation and/or strength training equipment may include non-movable portions onto which the user adds load. For example, to perform a leg-press-style exercise, the user may sit in a seat, place each of their feet on a respective foot plate, and push on the feet plate with their feet while the feet plate remain in the same position.

SUMMARY

Representative embodiments set forth herein disclose various techniques for enabling a system and method for improving completion of an exercise using an exercise machine. As used herein, the term "exercise machine" and "isometric exercise and rehabilitation assembly" may be used interchangeably. The term "exercise machine" and the term "isometric exercise and rehabilitation assembly" may also refer to an osteogenic, strength training, isometric exercise, and/or rehabilitation assembly.

In one embodiment, a method of a control system to improve compliance with an exercise plan for an exercise machine includes receiving one or more load measurements from one or more load cells of the exercise machine. The method also includes comparing the one or more load measurements to one or more target thresholds, and determining whether the one or more load measurements exceed the one or more target thresholds. Responsive to determining that the one or more load measurements exceed the one or more target thresholds, the method also includes causing a user interface to present an indication that the one or more target thresholds have been exceeded and an exercise is complete, wherein the exercise is included in the exercise plan.

In one embodiment, a method for presenting an indication to improve completion of an exercise plan for an exercise machine includes receiving, from a processing device of a control system, one or more load measurements obtained from one or more load cells included in the exercise machine. The method also includes presenting, in a user interface on a display screen, one or more visual representations for the one or more load measurements. The method also includes receiving an indication that an exercise is complete in the exercise plan based on the one or more load measurements having exceeded one or more target thresholds, and presenting, in the user interface with the one or more visual representations, the indication that the exercise is complete.

In one embodiment, a control system of an exercise machine includes a memory device storing instructions, and a processing device operatively coupled to the memory device. The processing device is configured to execute the instructions to receive one or more load measurements from one or more load cells of the exercise machine, compare the one or more load measurements to one or more target thresholds, and determine whether the one or more load measurements exceed the one or more target thresholds. Responsive to determining that the one or more load measurements exceed the one or more target thresholds, the processing device causes a user interface to present an indication that the one or more target thresholds have been exceeded and an exercise is complete, wherein the exercise is included in the exercise plan.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a detailed description of example embodiments, reference will now be made to the accompanying drawings in which:

FIG. 11 illustrates a side view of the second embodiment of the isometric exercise and rehabilitation assembly with a user performing a suitcase-lift-style exercise and a user interface presenting information to the user;

FIG. 13 illustrates a side view of the second embodiment of the isometric exercise and rehabilitation assembly with a user performing a leg-press-style exercise and a user interface presenting information to the user;

FIG. 15 illustrates a side view of the third embodiment of the isometric exercise and rehabilitation assembly with the user performing a pull-down-style exercise and a user interface presenting information to the user;

FIG. 16 illustrates a side view of the third embodiment of the isometric exercise and rehabilitation assembly with a user performing an arm-curl-style exercise and a user interface presenting information to the user;

FIG. 18 illustrates a side view of the third embodiment of the isometric exercise and rehabilitation assembly with a user performing a suitcase-lift-style exercise and a user interface presenting information to the user;

FIG. 20 illustrates example operations of another method for improving compliance with an exercise;

FIG. 21 illustrates example operations of yet another method for improving compliance with an exercise;

NOTATION AND NOMENCLATURE

Figure 1:
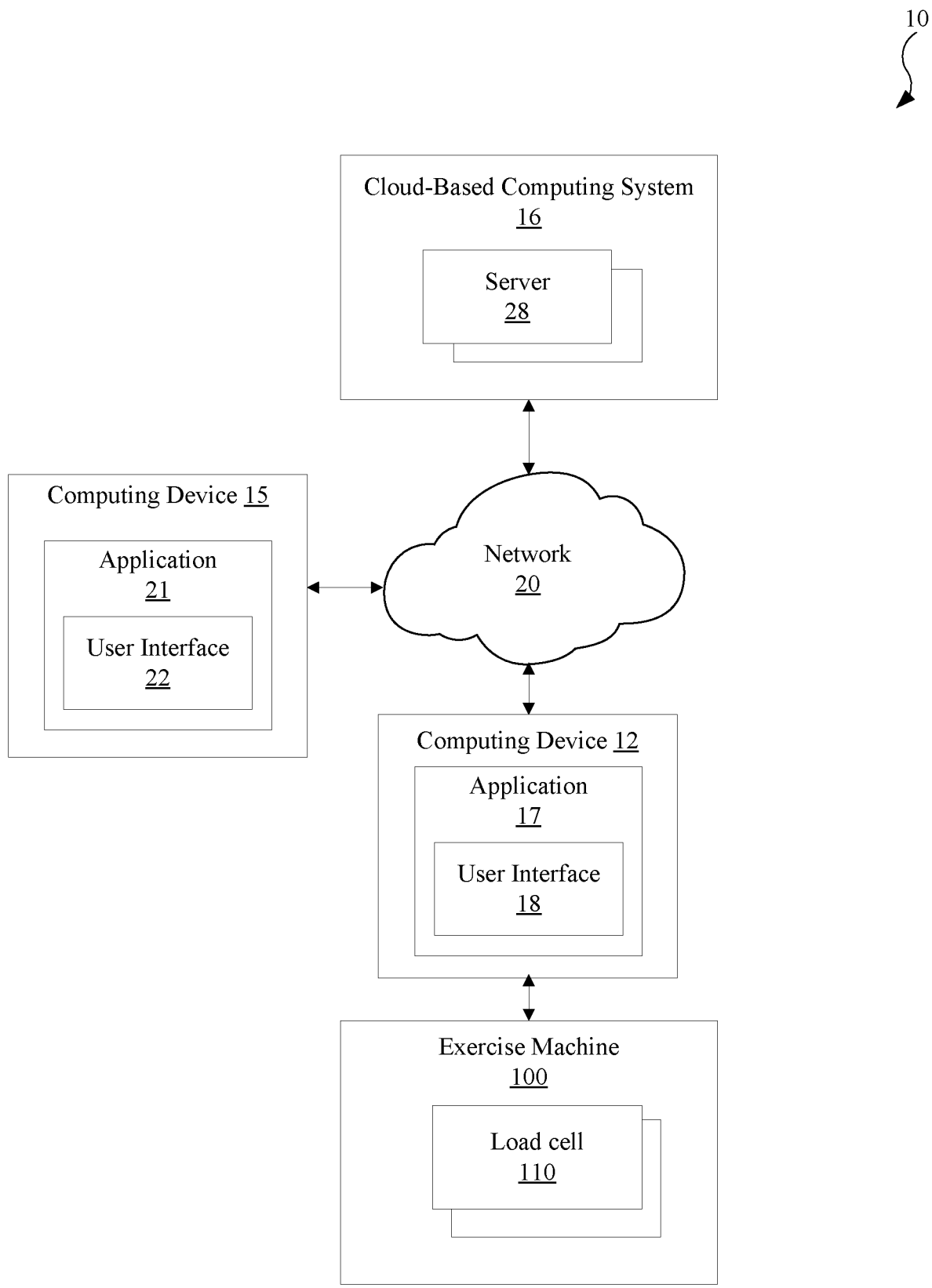
FIG. 1 illustrates a high-level component diagram of an illustrative system architecture according to certain embodiments of this disclosure.
Figure 2:
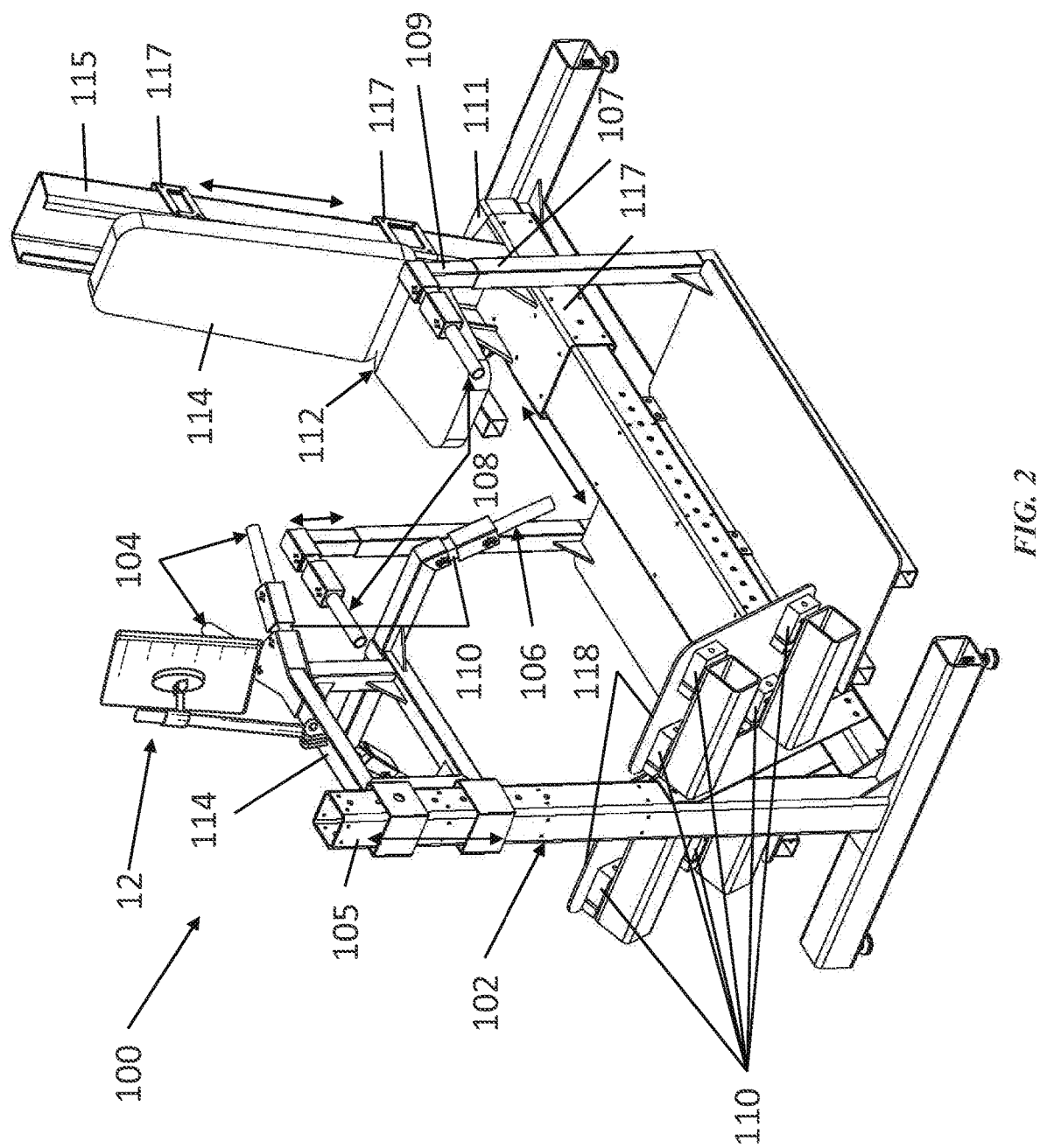
FIG. 2 illustrates an elevated perspective view of one embodiment of an isometric exercise and rehabilitation assembly.
Figure 3:
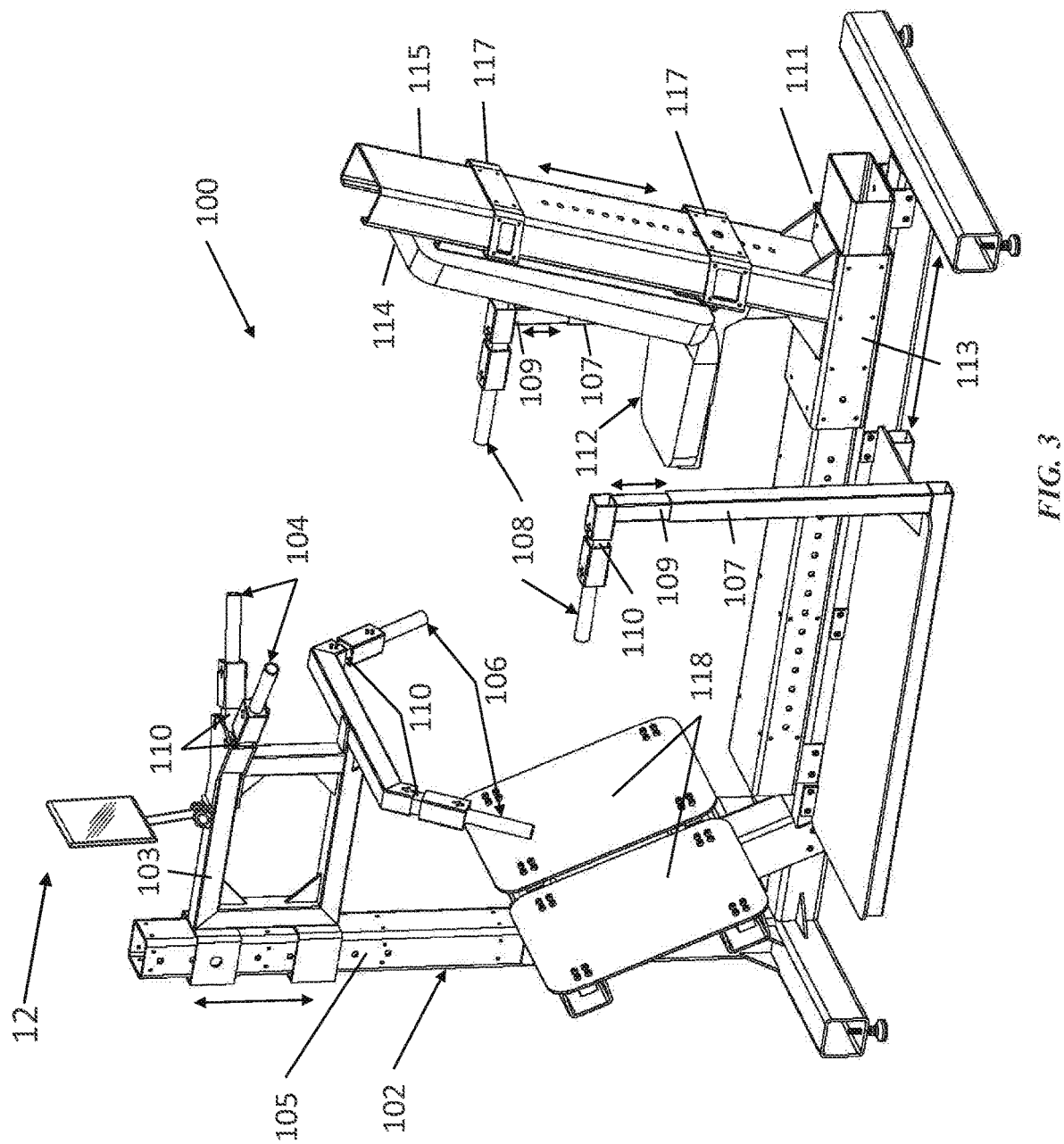
FIG. 3 illustrates a perspective view of the isometric exercise and rehabilitation assembly.
Figure 4:
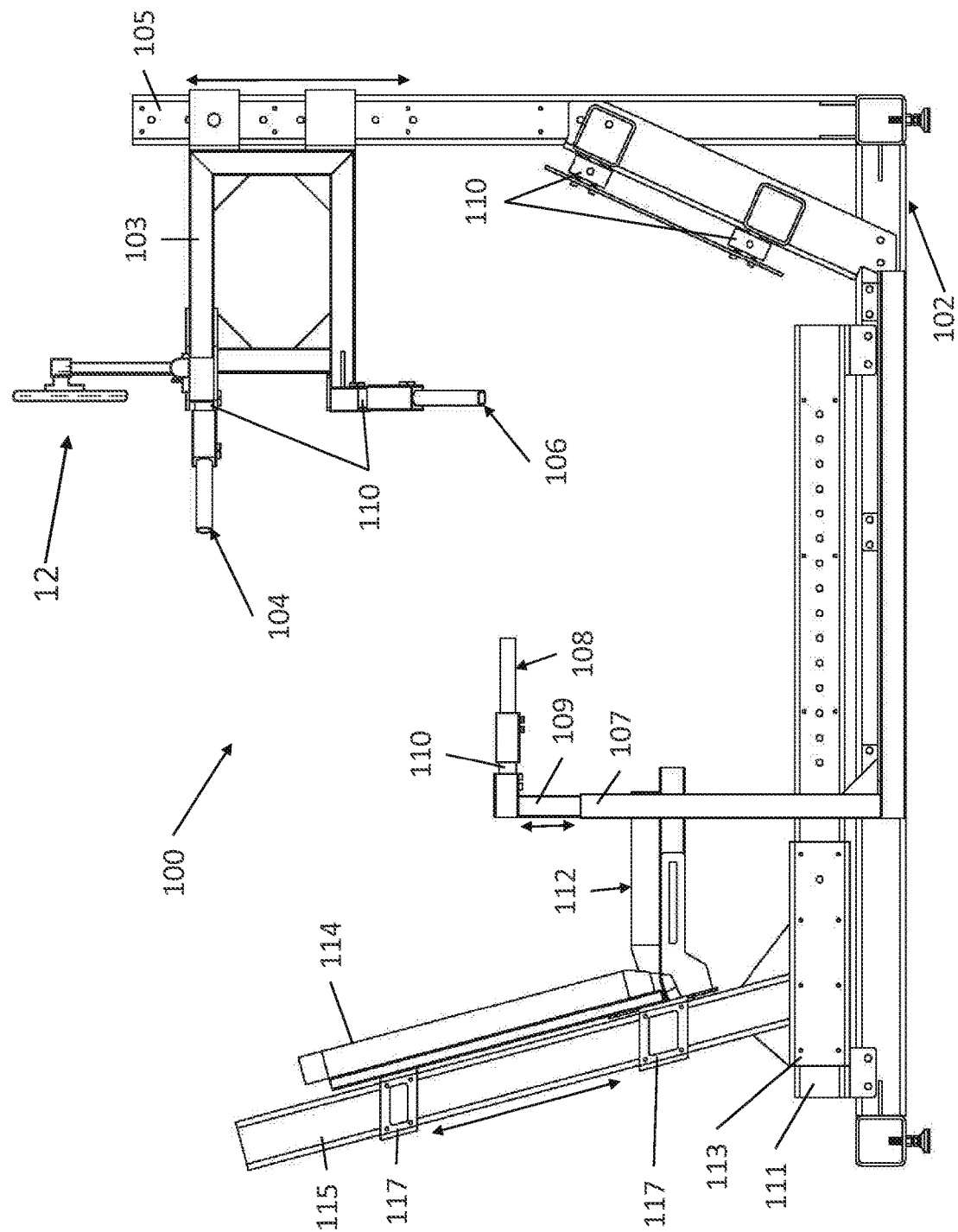
FIG. 4 illustrates a side view of the isometric exercise and rehabilitation assembly.
Figure 5:
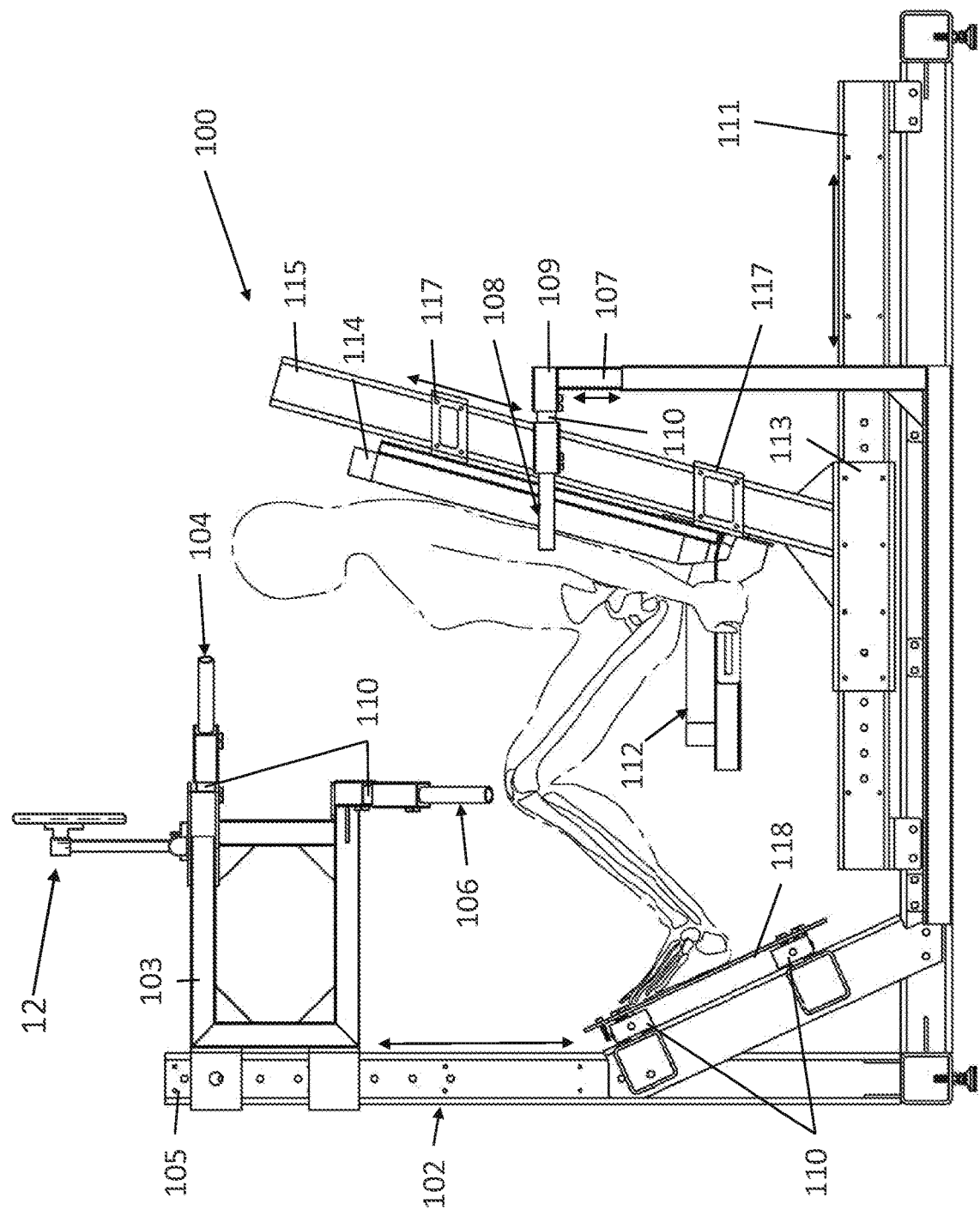
FIG. 5 illustrates a side view of the isometric exercise and rehabilitation assembly with a user performing a leg-press-style exercise.
Figure 6:
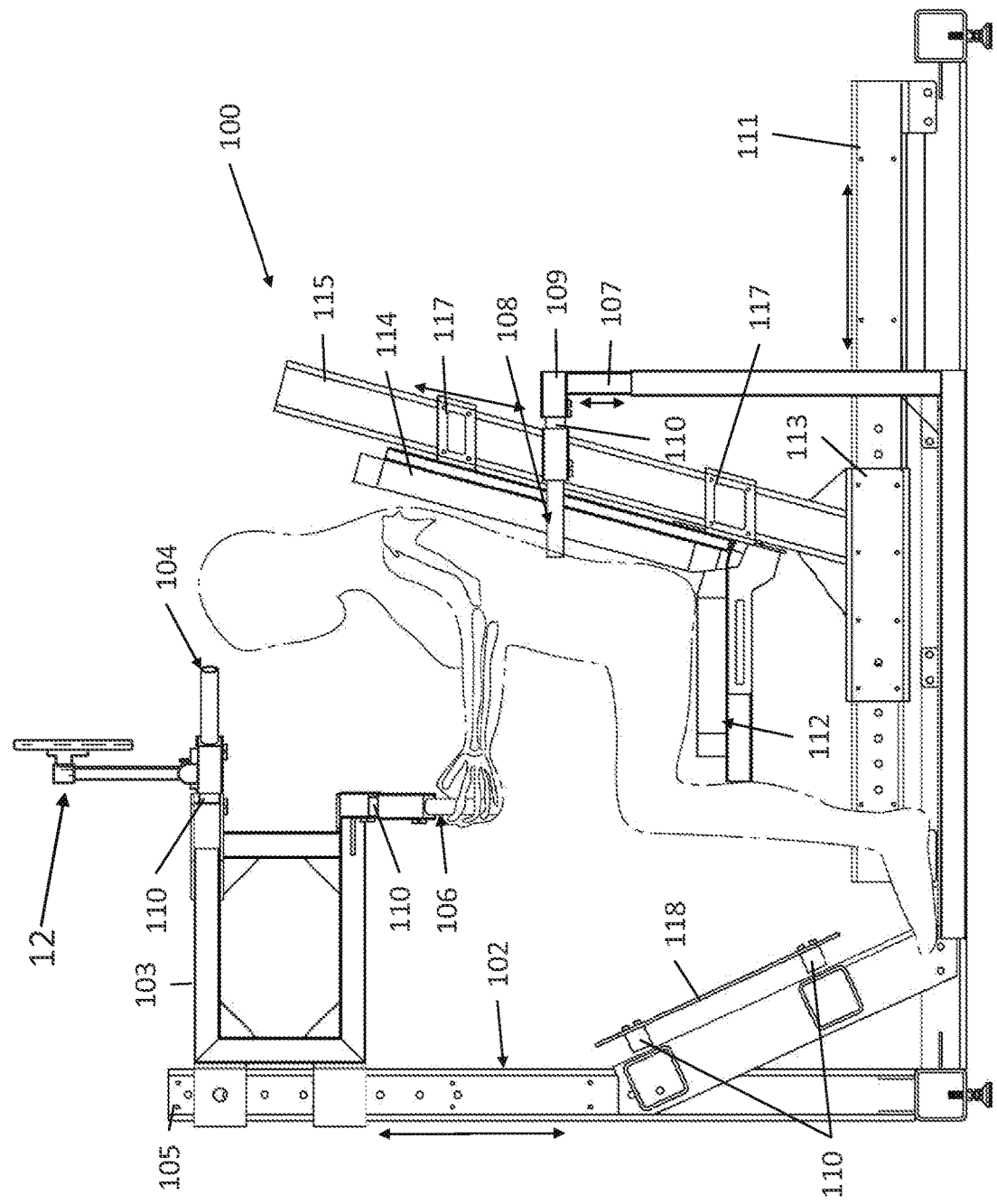
FIG. 6 illustrates a side view of the isometric exercise and rehabilitation assembly with a user performing a chest-press-style exercise.
Figure 7:
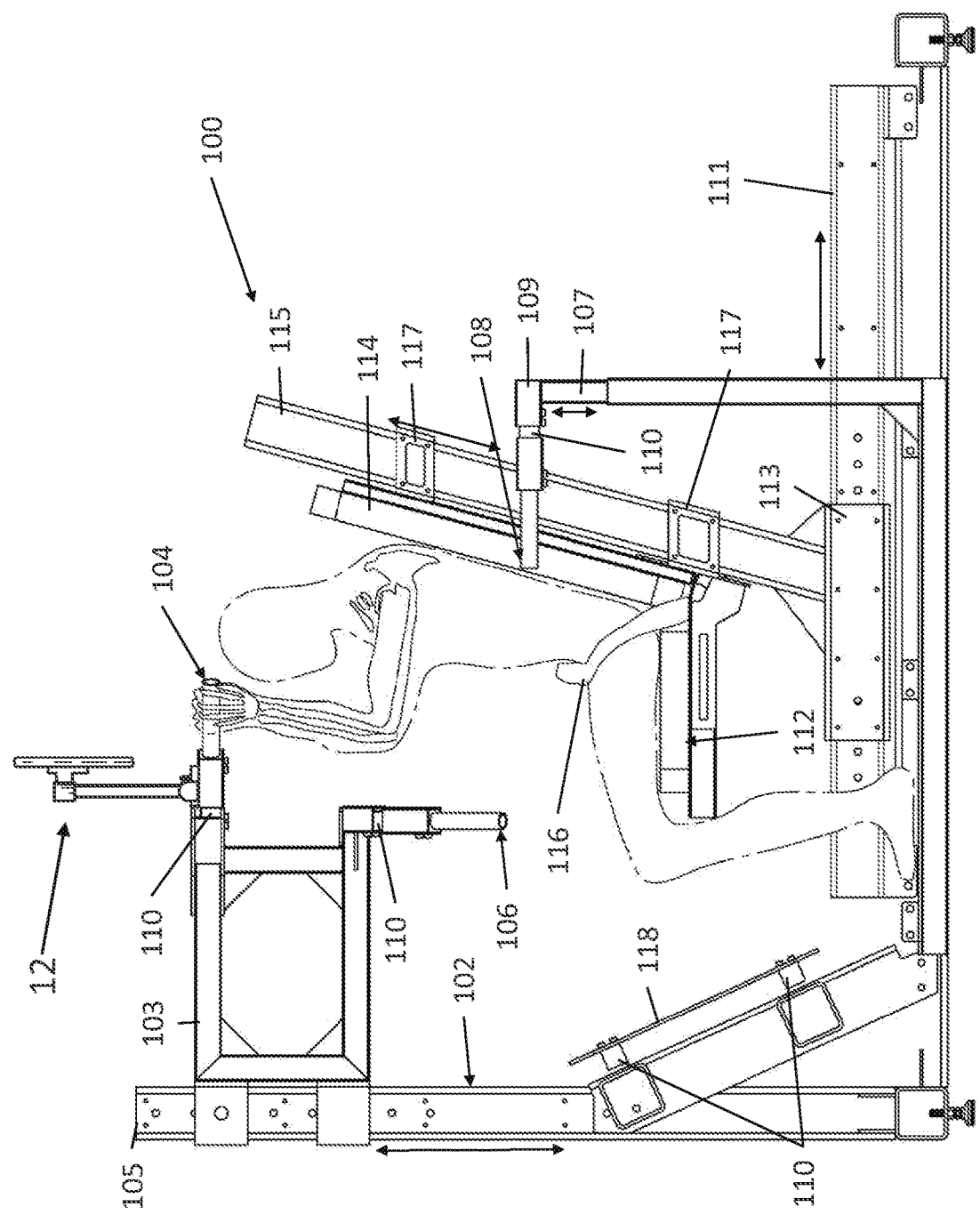
FIG. 7 illustrates a side view of the isometric exercise and rehabilitation assembly with a user performing a core-pull-style exercise.
Figure 8:
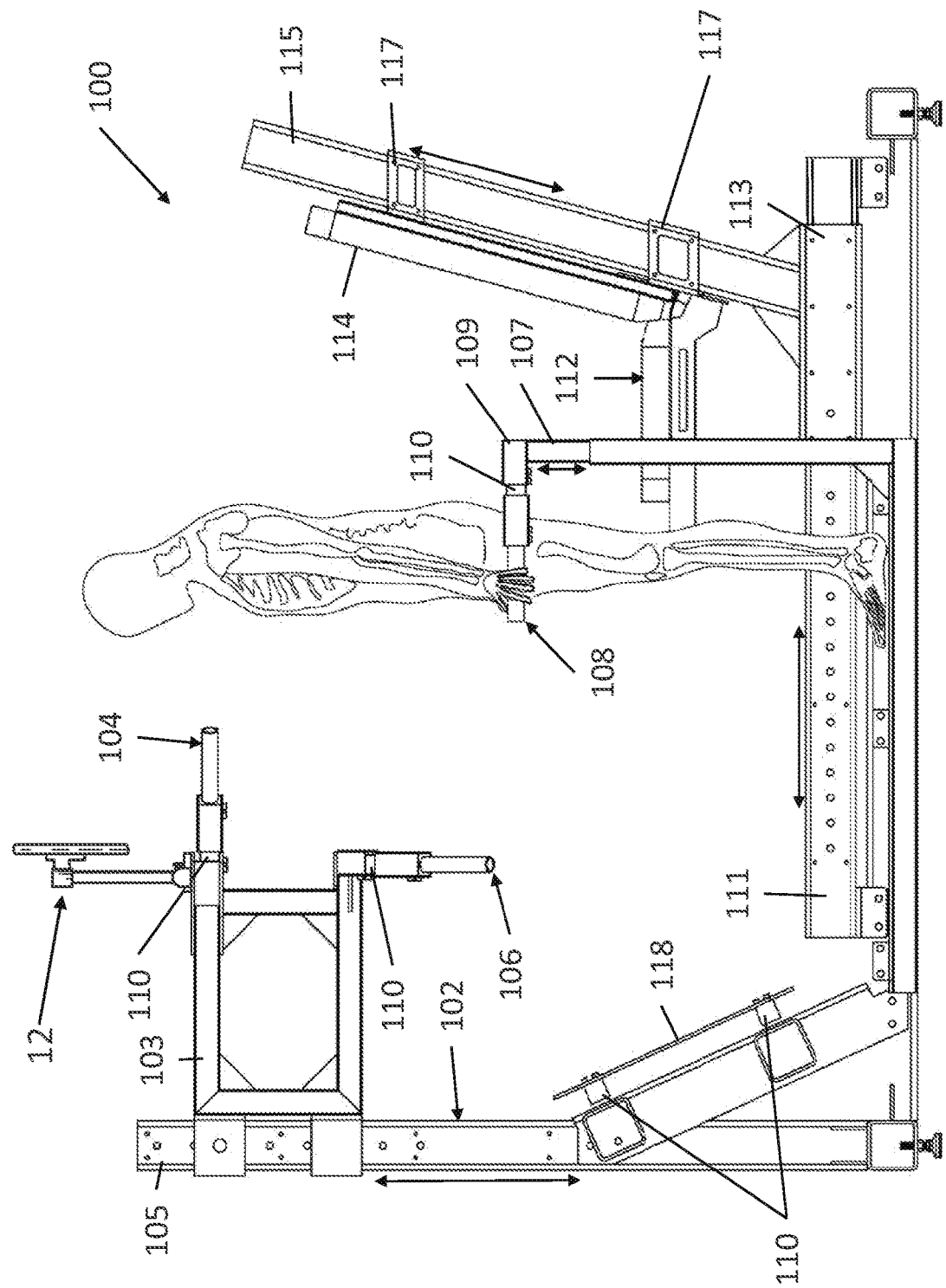
FIG. 8 illustrates a side view of the isometric exercise and rehabilitation assembly with a user performing a suitcase-lift-style exercise.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The subject matter of each of U.S. Pat. No. 10,226,663, issued Mar. 12, 2019; U.S. Pat. No. 10,173,094, issued Jan. 8, 2019; U.S. Pat. No. 10,173,095, issued Jan. 8, 2019; U.S. Pat. No. 10,173,096, issued Jan. 8, 2019; and U.S. Pat. No. 10,173,097, issued Jan. 8, 2019; and U.S. pending patent application Ser. No. 16/241,167 filed Jan. 7, 2019; Ser. No. 16/812,462 filed Mar. 9, 2020; Ser. No. 16/813,158 filed Mar. 9, 2020; Ser. No. 16/813,224 filed Mar. 9, 2020; and Ser. No. 16/813,303 filed Mar. 9, 2020, is incorporated herein by reference.

As typically healthy people grow from infants to children to adults, they experience bone growth. Such, growth, however, typically stops at approximately age 30. After that point, without interventions as described herein, bone loss (called osteoporosis), can start to occur. This does not mean that the body stops creating new bone. Rather, it means that the rate at which it creates new bone tends to slow, while the rate at which bone loss occurs tends to increase.

In addition, as people age and/or become less active than they once were, they may experience muscle loss. For example, muscles that are not used often may reduce in muscle mass. As a result, the muscles become weaker. In some instances, people may be affected by a disease, such as muscular dystrophy, that causes the muscles to become progressively weaker and to have reduced muscle mass. To increase the muscle mass and/or reduce the rate of muscle loss, people may exercise a muscle to cause muscular hypertrophy, thereby strengthening the muscle as the muscle grows. Muscular hypertrophy may refer to an increase in a size of skeletal muscle through a growth in size of its component cells. There are two factors that contribute to muscular hypertrophy, (i) sarcoplasmic hypertrophy (increase in muscle glycogen storage), and (ii) myofibrillar hypertrophy (increase in myofibril size). The growth in the cells may be caused by an adaptive response that serves to increase an ability to generate force or resist fatigue.

The rate at which such bone or muscle loss occurs generally accelerates as people age. A net growth in bone can ultimately become a net loss in bone, longitudinally across time. By the time, in general, women are over 50 and men are over 70, net bone loss can reach a point where brittleness of the bones is so great that the risk of life-altering fractures can occur. Examples of such fractures include fractures of the hip and femur. Of course, fractures can also occur due to participation in athletics or due to accidents. In such cases, it is just as relevant to have a need for bone growth which heals or speeds the healing of the fracture.

To understand why such fractures occur, it is useful to recognize that bone is itself porous, with a somewhat-honeycomb like structure. This structure may be dense and therefore stronger or it may be variegated, spread out and/or sparse, such latter structure being incapable of continuously or continually supporting the weight (load) stresses experienced in everyday living. When such loads exceed the support capability of the structure at a stressor point or points, a fracture occurs. This is true whether the individual had a fragile bone structure or a strong one: it is a matter of physics, of the literal "breaking point."

It is therefore preferable to have a means of mitigating or ameliorating bone loss and of healing fractures. Further, it is preferable to encourage new bone growth, thus increasing the density of the structure described hereinabove. The increased bone density may increase the load-bearing capacities of the bone, thus making first or subsequent fractures less likely to occur. Reduced fractures may improve a quality of life of the individual. The process of bone growth itself is referred to as osteogenesis, literally the creation of bone.

It is also preferable to have a means for mitigating or ameliorating muscle mass loss and weakening of the muscles. Further, it is preferable to encourage muscle growth by increasing the muscle mass through exercise. The increased muscle mass may enable a person to exert more force with the muscle and/or to resist fatigue in the muscle for a longer period of time.

In order to create new bone, at least three factors are necessary. First, the individual must have a sufficient intake of calcium, but second, in order to absorb that calcium, the individual must have a sufficient intake and absorption of Vitamin D, a matter problematic for those who have cystic fibrosis, who have undergone gastric bypass surgery or have other absorption disorders or conditions which limit absorption. Separately, supplemental estrogen for women and supplemental testosterone for men can further ameliorate bone loss. On the other hand, abuse of alcohol and smoking can harm one's bone structure. Medical conditions such as, without limitation, rheumatoid arthritis, renal disease, overactive parathyroid glands, diabetes or organ transplants can also exacerbate osteoporosis. Ethical pharmaceuticals such as, without limitation, hormone blockers, seizure medications and glucocorticoids are also capable of inducing such exacerbations. But even in the absence of medical conditions as described hereinabove, Vitamin D and calcium taken together do not create osteogenesis to a desirable degree or ameliorate bone loss to a desirable degree.

To achieve osteogenesis, therefore, one must add in the third factor: exercise. Specifically, one must subject one's bones to a force at least equal to certain multiple of body weight, such multiples varying depending on the individual and the specific bone in question. As used herein, "MOB" means Multiples of Body Weight. It has been determined through research that subjecting a given bone to a certain threshold MOB (this may also be known as a "weight-bearing exercise"), even for an extremely short period of time, one simply sufficient to exceed the threshold MOB, encourages and fosters osteogenesis in that bone.

Further, a person can achieve muscular hypertrophy by exercising the muscles for which increased muscle mass is desired. Strength training and/or resistance exercise may cause muscle tissue to increase. For example, pushing against or pulling on a stationary object with a certain amount of force may trigger the cells in the associated muscle to change and cause the muscle mass to increase.

The subject matter disclosed herein relates to a control system for an exercise machine, not only capable of enabling an individual, preferably an older, less mobile individual or preferably an individual recovering from a fracture, to engage easily in osteogenic exercises and/or muscle strengthening exercises, but capable of using predetermined thresholds or dynamically calculating them, such that the person using the machine can be immediately informed through real-time visual and/or other sensorial feedback, that the osteogenic threshold has been exceeded, thus triggering osteogenesis for the subject bone (or bones), and/or that the muscular strength threshold has been exceeded, thereby triggering muscular hypertrophy for the subject muscle (or muscles). The control system may be used to improve compliance with an exercise plan including one or more exercises.

The control system may receive one or more load measurements associated with forces exerted by both the left and right sides on left and right portions (e.g., handles, foot plate or platform) of the exercise machine to enhance osteogenesis, bone growth, bone density improvement, and/or muscle mass. The one or more load measurements may be a left load measurement of a load added to a left load cell on a left portion of the exercise machine and a right load measurement of a load added to a right load cell on a right portion of the exercise machine. A user interface may be provided by the control system that presents visual representations of the separately measured left load and right load where the respective left load and right load are added to the respective left load cell and right load cell at the subject portions of the exercise machine.

In some embodiments, initially, the control system may receive load measurements via a data channel associated with each exercise of the machine. For example, there may be a data channel for a leg-press-style exercise, a pull-down-style exercise, a suitcase-lift-style exercise, an arm-curl-style exercise, and so forth. Each data channel may include one or more load cells (e.g., a left load cell and a right load cell) that measure added load or applied force and transmit the load measurement to the control system via its respective data channel. The control system may receive the load measurements from each of the data channels at a first rate (e.g., 1 Hertz). If the control system detects a load from a data channel (e.g., hands resting on the handles including the respective load cells, or feet resting on the feet plate including the respective load cells), the control system may set that data channel as active and start reading load measurements from that data channel at a second rate (e.g., 10 Hertz) that is higher than the first rate. Further, the control system may set the other exercises associated with the other data channels as inactive and stop reading load measurements from the other data channels until the active exercise is complete. The active exercise may be complete when the one or more load measurements received via the data channel exceed one or more target thresholds. In some embodiments, the control system may determine an average load measurement by accumulating raw load measurements over a certain period of time (e.g., 5 seconds) and averaging the raw load measurements to smooth the data (e.g., eliminates jumps or spikes in data) in an average load measurement.

The control system may compare the one or more load measurements (e.g., raw load measurements, or averaged load measurements) to one or more target thresholds. In some embodiments, a single load measurement may be compared to a single specific target threshold (e.g., a one-to-one relationship). In some embodiments, a single load measurement may be compared to more than one specific target threshold (e.g., a one-to-many relationship). In some embodiments, more than one load measurement may be compared to a single specific target threshold (e.g., a many-to-one relationship). In some embodiments, more than one load measurement may be compared to more than one specific target threshold (e.g., a many-to-many relationship).

The target thresholds may be an osteopathic therapeutic target threshold and/or a muscular strength target threshold. The osteopathic therapeutic target threshold may be determined based on a disease protocol pertaining to the user, an age of the user, a gender of the user, a sex of the user, a height of the user, a weight of the user, a bone density of the user, etc. A disease protocol may refer to any illness, disease, fracture, or ailment experienced by the user and any treatment instructions provided by a caretaker for recovery and/or healing. The disease protocol may also include a condition of health where the goal is avoid a problem. The muscular strength target threshold may be determined based on a historical performance of the user using the exercise machine (e.g., amount of pounds lifted for a particular exercise, amount of force applied associated with each body part, etc.) and/or other exercise machines, a fitness level (e.g., how active the user is) of the user, a diet of the user, a protocol for determining a muscular strength target, etc.

The control system may determine whether the one or more load measurements exceed the one or more target thresholds. Responsive to determining that the one or more load measurements exceed the one or more target thresholds, the control system may cause a user interface to present an indication that the one or more target thresholds have been exceeded and an exercise is complete. Additionally, when the one or more target thresholds are exceeded, the control system may cause the user interface to present an indication that instructs the user to apply additional force (less than a safety limit) to attempt to set a personal maximum record of weight lifted, pressed, pulled, or otherwise exert force thereupon for that exercise.

Further, the user interface may present an indication when a load measurement is approaching a target threshold for the user. In another example, when the load measurement exceeds the target threshold, the user interface may present an indication that the target threshold has been exceeded, that the exercise is complete, and if there are any remaining incomplete exercises in the exercise plan, that there is another exercise to be completed by the user. If there are no remaining exercises in the exercise plan to complete, then the user interface may present an indication that all exercises in the exercise plan are complete and the user can rest. In addition, when the exercise plan is complete, the control system may generate a performance report that presents various information (e.g., charts and graphs of the right and left load measurements received during each of the exercises, left and right maximum loads for the user received during each of the exercises, historical right and left load measurements received in the past, comparison of the current right and left load measurements with the historical right and left load measurement, an amount of pounds lifted or pressed that is determined based on the load measurements for each of the exercises, percent gained in load measurements over time, etc.).

Further, the one or more load measurements may each be compared to a safety limit. For example, a left load measurement and a right load measurement may each be compared to the safety limit for the user. The safety limit may be determined for the user based on the user's disease protocol. There may be different safety limits for different portions of the user's body on the left and the right side, one extremity versus another extremity, a top portion of the user's body and a body portion of the user's body, etc., and for different exercises. For example, if someone underwent left knee surgery, the safety limit for a user for a left load measurement for a leg-press-style exercise may be different from the safety limit for a right load measurement for that exercise and user. If the safety limit is exceeded, an indication may be presented on the user interface to instruct to reduce the amount of force the user is applying and/or to instruct the user to stop applying force because the safety limit is exceeded.

For those with any or all of the osteoporosis-exacerbating medical conditions described herein, such a control system and exercise machine can slow the rate of net bone loss by enabling osteogenesis to occur without exertions which would not be possible for someone whose health is fragile, not robust. Another benefit of the present disclosure, therefore, is its ability to speed the healing of fractures in athletically robust individuals. Further, another benefit is the increase in muscle mass by using the exercise machine to trigger muscular hypertrophy. The control system may provide an automated interface that improves compliance with an exercise plan by using a real-time feedback loop to measure loads added during each of the exercises, compare the load measurements to target thresholds and/or safety limits that are uniquely determined for the user using the exercise machine, and provide various indications based on the comparison. For example, the indications pertain to when the user should add more load, when the target thresholds are exceeded, when the safety limit is exceeded, when the exercise is complete, when the user should begin another exercise, and so forth.

Bone Exercises and their Benefits

The following exercises achieve bone strengthening results by exposing relevant parts of a user to isometric forces which are selected multiples of body weight (MOB) of the user, a threshold level above which bone mineral density increases. A MOB may be any fraction or rational number excluding zero. The specific MOB-multiple threshold necessary to effect such increases will naturally vary from individual to individual and may be more or less for any given individual. "Bone-strengthening," as used herein, specifically includes, without limitation, a process of osteogenesis, whether due to the creation of new bone as a result of an increase in the bone mineral density; or proximately to the introduction or causation of microfractures in the underlying bone. The exercises referred to are as follows.

Leg Press

A leg-press-style exercise to improve isometric muscular strength in the following key muscle groups: gluteals, hamstrings, quadriceps, spinal extensors and grip muscles as well as to increase resistance to skeletal fractures in leg bones such as the femur. In one example, the leg-press-style exercise can be performed approximately 4.2 MOB or more of the user.

Chest Press

A chest-press-style exercise to improve isometric muscular strength in the following key muscle groups: pectorals, deltoids, and tricep and grip muscles as well as in increasing resistance to skeletal fractures in the humerus, clavicle, radial, ulnar and rib pectoral regions. In one example, the chest-press-style exercise can be performed at approximately 2.5 MOB or more of the user.

Suitcase Lift

A suitcase-lift-style exercise to improve isometric muscular strength in the following key muscle groups: gluteals, hamstrings, quadriceps, spinal extensors, abdominals, and upper back and grip muscles as well as to increase resistance to skeletal fractures in the femur and spine. In one example, the suitcase-lift-style exercise can be performed at approximately 2.5 MOB or more of the user.

Arm Curl

An arm-curl-style exercise to improve isometric muscular strength in the following key muscle groups: biceps, brachialis, brachioradialis, grip muscles and trunk as well as in increasing resistance to skeletal fractures in the humerus, ribs and spine. In one example, the arm-curl-style exercise can be performed at approximately 1.5 MOB or more of the user.

Core Pull

A core-pull-style exercise to improve isometric muscular strength in the following key muscle groups: elbow flexors, grip muscles, latissimus dorsi, hip flexors and trunk as well as in increasing resistance to skeletal fractures in the ribs and spine. In one example, the core-pull-style exercise can be performed at approximately 1.5 MOB or more of the user.

Grip Strength

A grip-strengthening-style exercise which may preferably be situated around a station in an exercise machine, in order to improve strength in the muscles of the hand and forearm. Grip strength is medically salient because it has been positively correlated with better states of health.

In some embodiments, a balance board may be communicatively coupled to the control system. For example, the balance board may include a network interface that communicates with the control system via any suitable interface protocol (e.g., Bluetooth, WiFi, cellular). The balance board may include pressure sensors and may obtain measurements of locations and amount of pressure applied to the balance board. The measurements may be transmitted to the control system. The control system may present a game or interactive exercise on a user interface. The game or interactive exercise may modify screens or adjust graphics that are displayed based on the measurements received from the balance board. The balance board may be used by a user to perform any suitable type of plank (e.g., knee plank, regular feet and elbow plank, table plank with elbows, or the like). Accordingly, the balance board may be configured to be used with arms on the balance board, knees on the balance board, and/or feet standing on the balance board. The games or interactive exercises may encourage the user during the game or interactive exercises to increase compliance and neuro-motor control after a surgery, for example.

The exercise machine, balance board, wristband, goniometer, and/or any suitable accessory may be used for various reasons in various markets. For example, users may use the exercise machine, balance board, wristband, goniometer, and/or any suitable accessory in the orthopedic market if the users suffer from chronic musculosketal pain (e.g., knees, hips, shoulders, and back). The exercise machine, balance board, wristband, goniometer, and/or any suitable accessory may be used to help with prehabilitation (prehab), as well as optimize post-surgical outcomes. Users may use the exercise machine, balance board, wristband, goniometer, and/or any suitable accessory in the back and neck pain market if the users suffer with chronic back and neck pain and they want to avoid surgery and experience long-term relief, as well as users that are in recovery following surgery. Users may use the exercise machine, balance board, wristband, goniometer, and/or any suitable accessory in the cardiovascular market if they desire to prevent or recover from life-threatening cardiovascular disease, especially heart attacks and stroke. Users may use the exercise machine, balance board, wristband, goniometer, and/or any suitable accessory in the neurological market if they desire to recover from stroke, or have conditions like Parkinson's Disease and/or Multiple Sclerosis, and the users desire to achieve better balance, strength, and muscle symmetry in order to slow progression of the medical condition.

The following discussion is directed to various embodiments of the present disclosure. Although these embodiments are given as examples, the embodiments disclosed should not be interpreted, or otherwise used, as limiting the scope of the disclosure, including the claims. In addition, one of ordinary skill in the art will understand that the following description has broad application, and the discussion of any embodiment is meant only to be exemplary of that embodiment, and not intended to intimate that the scope of the disclosure, including the claims, is limited to that embodiment.

FIG. 1 illustrates a high-level component diagram of an illustrative system architecture 10 according to certain embodiments of this disclosure. In some embodiments, the system architecture 10 may include a computing device 12 communicatively coupled to an exercise machine 100. The computing device 12 may also be communicatively coupled with a computing device 15 and a cloud-based computing system 16. As used herein, a cloud-based computing system refers, without limitation, to any remote or distal computing system accessed over a network link. Each of the computing device 12, computing device 15, and/or the exercise machine 100 may include one or more processing devices, memory devices, and network interface devices. In some embodiments, the computing device 12 may be included as part of the structure of the exercise machine 100. In some embodiments, the computing device 12 may be separate from the exercise machine 100. For example, the computing device 12 may be a smartphone, tablet, laptop, or the like.

The network interface devices may enable communication via a wireless protocol for transmitting data over short distances, such as Bluetooth, ZigBee, near field communication (NFC), etc. In some embodiments, the computing device 12 is communicatively coupled to the exercise machine 100 via Bluetooth. Additionally, the network interface devices may enable communicating data over long distances, and in one example, the computing device 12 may communicate with a network 20. Network 20 may be a public network (e.g., connected to the Internet via wired (Ethernet) or wireless (WiFi)), a private network (e.g., a local area network (LAN), wide area network (WAN), virtual private network (VPN)), or a combination thereof.

The computing device 12 may be any suitable computing device, such as a laptop, tablet, smartphone, or computer. The computing device 12 may include a display that is capable of presenting a user interface 18 of an application 17. The application 17 may be implemented in computer instructions stored on the one or more memory devices of the computing device 12 and executable by the one or more processing devices of the computing device 12. The application 17 may be a stand-alone application that is installed on the computing device 12 or may be an application (e.g., website) that executes via a web browser. The user interface 18 may present various screens to a user that enable the user to login, enter personal information (e.g., health information; a disease protocol prescribed by a physician, trainer, or caretaker; age; gender; activity level; bone density; weight; height; patient measurements; etc.), view an exercise plan, initiate an exercise in the exercise plan, view visual representations of left load measurements and right load measurements that are received from left load cells and right load cells during the exercise, view a weight in pounds that are pushed, lifted, or pulled during the exercise, view an indication when the user has almost reached a target threshold, view an indication when the user has exceeded the target thresholds, view an indication when the user has set a new personal maximum for a load measurement and/or pounds pushed, lifted, or pulled, view an indication when a load measurement exceeds a safety limit, view an indication to instruct the user to begin another exercise, view an indication that congratulates the user for completing all exercises in the exercise plan, and so forth, as described in more detail below. The computing device 12 may also include instructions stored on the one or more memory devices that, when executed by the one or more processing devices of the computing device 12, perform operations to control the exercise machine 100.

The computing device 15 may execute an application 21. The application 21 may be implemented in computer instructions stored on the one or more memory devices of the computing device 15 and executable by the one or more processing devices of the computing device 15. The application 21 may present a user interface 22 including various screens to a physician, trainer, or caregiver that enable the person to create an exercise plan for a user based on a treatment (e.g., surgery, medical procedure, etc.) the user underwent and/or injury (e.g., sprain, tear, fracture, etc.) the user suffered, view progress of the user throughout the exercise plan, and/or view measured properties (e.g., force exerted on portions of the exercise machine 100) of the user during exercises of the exercise plan. The exercise plan specific to a patient may be transmitted via the network 20 to the cloud-based computing system 16 for storage and/or to the computing device 12 so the patient may begin the exercise plan. The exercise plan may specifying one or more exercises that are available at the exercise machine 100.

The exercise machine 100 may be an osteogenic, muscular strengthening, isometric exercise and/or rehabilitation assembly. Solid state, static, or isometric exercise and rehabilitation equipment (e.g., exercise machine 100) can be used to facilitate osteogenic exercises that are isometric in nature and/or to facilitate muscular strengthening exercises. Such exercise and rehabilitation equipment can include equipment in which there are no moving parts while the user is exercising. While there may be some flexing under load, incidental movement resulting from the tolerances of interlocking parts, and parts that can move while performing adjustments on the exercise and rehabilitation equipment, these flexions and movements can comprise, without limitation, exercise and rehabilitation equipment from the field of isometric exercise and rehabilitation equipment.

The exercise machine 100 may include various load cells 110 disposed at various portions of the exercise machine 100. For example, one or more left load cells 110 may be located at one or more left feet plates or platforms, and one or more right load cells may be located at one or more right feet plates or platforms. Also, one or more left load cells may be located at one or more left handles, and one or more right load cells may be located at one or more right handles. Each exercise in the exercise system may be associated with both a left and a right portion (e.g., handle or foot plate) of the exercise machine 100. For example, a leg-press-style exercise is associated with a left foot plate and a right foot plate. The left load cell at the left foot plate and the right load cell at the right foot plate may independently measure a load added onto the left foot plate and the right foot plate, respectively, and transmit the left load measurement and the right load measurement to the computing device 12. The load added onto the load cells 110 may represent an amount of weight added onto the load cells. In some embodiments, the load added onto the load cells 110 may represent an amount of force exerted by the user on the load cells. Accordingly, the left load measurement and the right load measurement may be used to present a left force (e.g., in Newtons) and a right force (e.g., in Newtons). The left force and right force may be totaled and converted into a total weight in pounds for the exercise. Each of the left force, the right force, and/or the total weight in pounds may be presented on the user interface 18.

In some embodiments, the cloud-based computing system 16 may include one or more servers 28 that form a distributed, grid, and/or peer-to-peer (P2P) computing architecture. Each of the servers 28 may include one or more processing devices, memory devices, data storage, and/or network interface devices. The servers 28 may be in communication with one another via any suitable communication protocol. The servers 28 may store profiles for each of the users that use the exercise device 100. The profiles may include information about the users such as one or more disease protocols, one or more exercise plans, a historical performance (e.g., loads applied to the left load cell and right load cell, total weight in pounds, etc.) for each type of exercise that can be performed using the exercise machine 100, health, age, race, credentials for logging into the application 17, and so forth.

FIGS. 2-8 illustrates one or more embodiments of an osteogenic, isometric exercise and rehabilitation assembly. An aspect of the disclosure includes an isometric exercise and rehabilitation assembly 100. The assembly 100 can include a frame 102. The assembly can further include one or more pairs of load handles 104, 106, 108 (e.g., three shown) supported by the frame 102. Each load handle in one of the pairs of load handles 104, 106, 108 can be symmetrically spaced from each other relative to a vertical plane of the assembly 100. For example, the vertical plane can bisect the assembly 100 in a longitudinal direction.

During exercise, a user can grip and apply force to one of the pairs of load handles 104, 106, 108. The term "apply force" can include a single force, more than one force, a range of forces, etc. and may be used interchangeably with "addition of load". Each load handle in the pairs of load handles 104, 106, 108 can include at least one load cell 110 for separately and independently measuring a force applied to, or a load added onto, respective load handles. Further, each foot plate 118 (e.g., a left foot plate and a right foot plate) can include at least one load cell 110 for separately and independently measuring a force applied to, or a load added onto, respective foot plates.

The placement of a load cell 110 in each pair of load handles 104, 106, 108 and/or feet plates 118 can provide the ability to read variations in force applied between the left and right sides of the user. This allows a user or trainer to understand relative strength. This is also useful in understanding strength when recovering from an injury.

In some embodiments, the assembly further can include the computing device 12. One or more of the load cells 110 can be individually in electrical communication with the computing device 12 either via a wired or wireless connection. In some embodiments, the user interface 18 presented via a display of the computing device 12 may indicate how to perform an exercise, how much force is being applied, a target force to be applied, historical information for the user about how much force they applied at prior sessions, comparisons to averages, etc., as well as additional information, recommendations, notifications, and/or indications described herein.

In some embodiments, the assembly further includes a seat 112 supported by the frame 102 in which a user sits while applying force to the load handles and/or feet plates. In some embodiments, the seat 112 can include a support such as a backboard 114. In some embodiments, the position of the seat 112 is adjustable in a horizontal and/or vertical dimension. In some embodiments, the angle of the seat 112 is adjustable. In some embodiments, the angle of the backboard 114 is adjustable. Examples of how adjustments to the seat 112 and backboard 112 can be implemented include, but are not limited to, using telescoping tubes and pins, hydraulic pistons, electric motors, etc. In some embodiments, the seat 112 can further include a fastening system 116 (FIG. 7), such as a seat belt, for securing the user to the seat 112.

In one example, the seat 112 can include a base 113 that is slidably mounted to a horizontal rail 111 of the frame 102. The seat 112 can be selectively repositionable and secured as indicated by the double-headed arrow. In another example, the seat 112 can include one or more supports 117 (e.g., two shown) that are slidably mounted to a substantially vertical rail 115 of the frame 102. The seat 112 can be selectively repositionable and secured as indicated by the double-headed arrow.

In some embodiments, a pair of feet plate 118 can be located angled toward and in front of the seat 112. The user can apply force to the feet plate 118 (FIG. 5) while sitting in the seat 112 during a leg-press-style exercise. The leg-press-style exercise can provide or enable osteogenesis, bone growth or bone density improvement for a portion of the skeletal system of the user. Further, the leg-press-style exercise can provide or enable muscular hypertrophy for one or more muscles of the user. In a leg-press-style exercise, the user can sit in the seat 112, place their feet on respective feet plates 118, and push on the pair of feet plate 118 using their legs.

In some embodiments, adjustments can be made to the position of the pair of feet plate 118. For example, these adjustments can include the height of the pair of feet plate 118, the distance between the pair of feet plate 118 and the seat 112, the distance between each handle of the pair of feet plate 118, the angle of the pair of feet plate 118 relative to the user, etc. In some embodiments, to account for natural differences in limb length or injuries, each foot plate of the pair of feet plate 118 can be adjusted separately.

In some embodiments, a first pair of load handles 104 can be located above and in front of the seat 112. The user can apply force to the load handles 104 (FIG. 7) while being constrained in the seat 112 by the fastening system 116 in a core-pull-style exercise. The core-pull-style exercise can provide or enable osteogenesis, bone growth or bone density improvement for a portion of the skeletal system of the user. Further, the core-pull-style exercise can provide or enable muscular hypertrophy for one or more muscles of the user. In a core-pull-style exercise, while the lower body of the user is restrained from upward movement by the fastening system 116, the user can sit in the seat 112, apply the fastening system 116, hold the first pair of load handles 104, and pull on the first pair of load handles 104 using their arms.

In some embodiments, adjustments can be made to the position of the first pair of load handles 104. For example, these adjustments can include the height of the first pair of load handles 104, the distance between the first pair of load handles 104 and the seat 112, the distance between each handle of the first pair of load handles 104, the angle of the first load handles 104 relative to the user, etc. In some embodiments, to account for natural differences in limb length or injuries, each handle of the first pair of load handles 104 can be adjusted separately.

In one example, the first pair of load handles 104 can include a sub-frame 103 that is slidably mounted to a vertical rail 105 of the frame 102. The first pair of load handles 104 can be selectively repositionable and secured as indicated by the double-headed arrow.

In some embodiments, a second pair of load handles 106 can be spaced apart from and in the front of the seat 112. While seated (FIG. 6), the user can apply force to the second pair of load handles 106 in a chest-press-style exercise. The chest-press-style exercise can provide or enable osteogenesis, bone growth or bone density improvement for another portion of the skeletal system of the user. Further, the chest-press-style exercise can provide or enable muscular hypertrophy for one or more muscles of the user. In a chest-press-style exercise, the user can sit in the seat 112, hold the second pair of load handles 106, and push against the second pair of load handles 106 with their arms.

In some embodiments, adjustments can be made to the position of the second pair of load handles 106. These adjustments can include the height of the second pair of load handles 106, the distance between the second pair of load handles 106 and the seat 112, the distance between each handle of the second pair of load handles 106, the angle of the second load handles 106 relative to the user, etc. In some embodiments, to account for natural differences in limb length or injuries, each handle of the second pair of load handles 106 can be adjusted separately.

In one example, the second pair of load handles 106 can include the sub-frame 103 that is slidably mounted to the vertical rail 105 of the frame 102. The sub-frame 103 can be the same sub-frame 103 provided for the first pair of load handles 104, or a different, independent sub-frame. The second pair of load handles 106 can be selectively repositionable and secured as indicated by the double-headed arrow.

In some embodiments (FIG. 8), a third pair of load handles 108 can be located immediately adjacent the seat 112, such that the user can stand and apply force in a suitcase-lift-style exercise. The suitcase-lift-style exercise can provide or enable osteogenesis, bone growth or bone density improvement for still another portion of the skeletal system of the user. Further, the suitcase-lift-style exercise can provide or enable muscular hypertrophy for one or more muscles of the user. Examples of the third pair of load handles 108 can extend horizontally along a pair of respective axes that are parallel to the vertical plane. The third pair of load handles 108 can be horizontally co-planar, such that a user can apply force to them in a suitcase-lift-style exercise. In the suitcase-lift-style exercise, the user can stand on the floor or a horizontal portion of the frame 102, bend their knees, grip the third pair of load handles 108, and extend their legs to apply an upward force to the third pair of load handles 108.

In some embodiments, adjustments can be made to the position of the third pair of load handles 108. These adjustments can include the height of the third pair of load handles 108, the distance between the third pair of load handles 108 and the seat 112, the distance between each handle of the third pair of load handles 108, the angle of the third load handles 108 relative to the user, etc. In some embodiments, to account for natural differences in limb length or injuries, each handle of the third pair of load handles 108 can be adjusted separately.

In one example, each load handle 108 of the third pair of load handles 108 can include a sub-frame 109 that is slidably mounted in or to a vertical tube 107 of the frame 102. Each load handle 108 of the third pair of load handles 108 can be selectively repositionable and secured as indicated by the double-headed arrows.

In other embodiments (not shown), the third pair of load handles 108 can be reconfigured to be coaxial and located horizontally in front of the user along an axis that is perpendicular to the vertical plane. The user can apply force to the third pair of load handles 108 in a deadlift-style exercise. Like the suitcase-lift-style exercise, the deadlift-style exercise can provide or enable osteogenesis, bone growth or bone density improvement for a portion of the skeletal system of the user. Further, the deadlift-style exercise can provide or enable muscular hypertrophy for one or more muscles of the user. In the deadlift-style exercise, the user can stand on the floor or a horizontal portion of the frame 102, bend their knees, hold the third pair of load handles 108 in front of them, and extend their legs to apply an upward force to the third pair of load handles 108. In some embodiments, the third pair of load handles 108 can be adjusted (e.g., rotated) from the described coaxial position used for the deadlift-style exercise, to the parallel position (FIGS. 7, 8) used for the suitcase lift-style exercise. The third pair of load handles 108, or others, can be used in a grip strengthening-style exercise to improve strength in the muscles of the hand and forearm.

Figure 9:
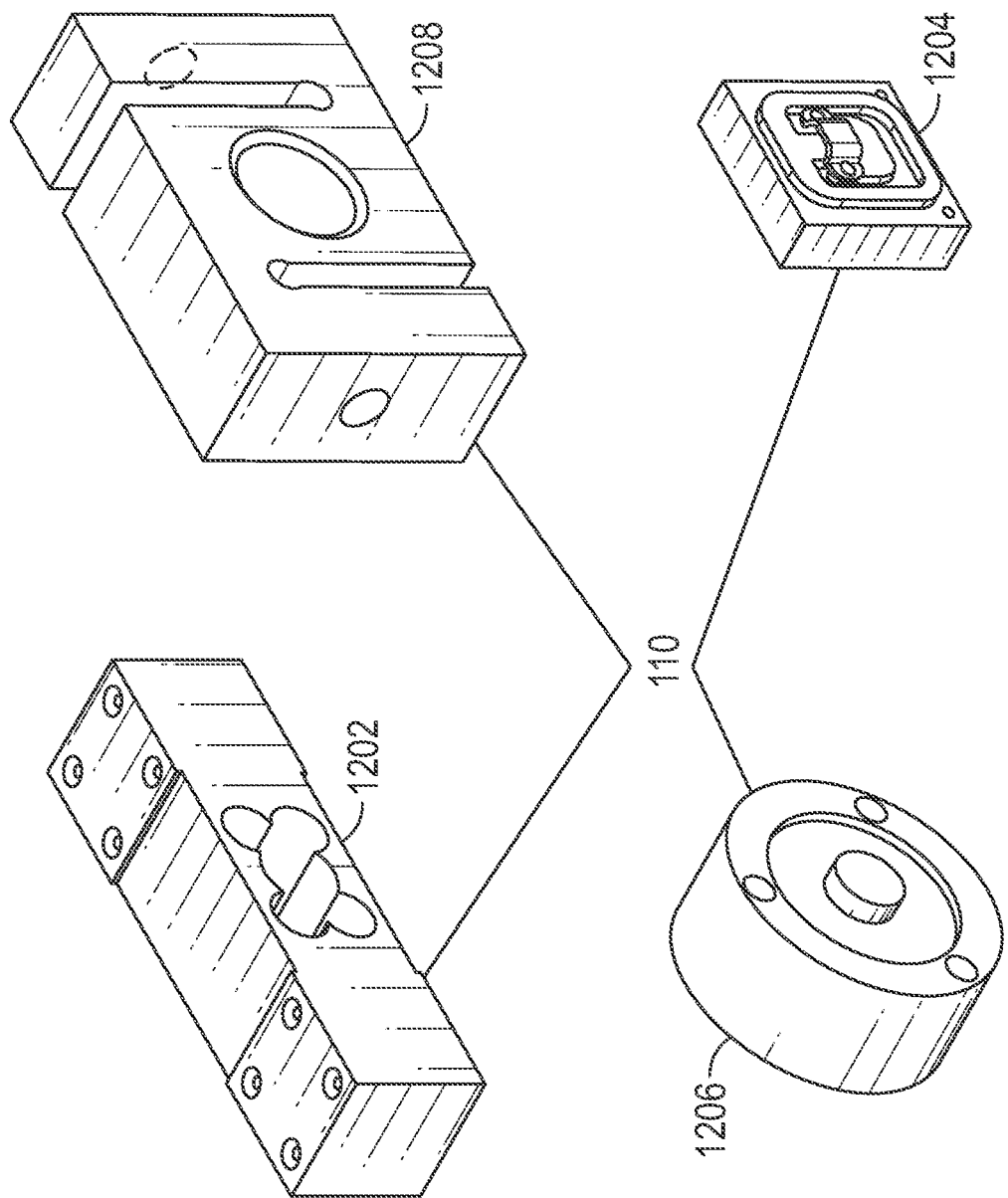
FIG. 9 illustrates four examples of load cells that can be used in the isometric exercise assembly.

FIG. 9 depicts several options for the load cells 110. In some embodiments, the load cells 110 can be piezoelectric load cells, such as PACEline CLP Piezoelectric Subminiature Load Washers. In other embodiments, the load cells 110 can be hydraulic load cells, such as NOSHOK hydraulic load cells. In some versions, the load cells 110 can include strain gauges. Embodiments of the strain gauges can be bending-type strain gauges, such as Omega SGN-4/20-PN 4 mm grid, 20 ohm nickel foil resistors. Other examples of the strain gauges can be double-bending-type strain gauges 1202, such as Rudera Sensor RSL 642 strain gauges. Still other embodiments of the strain gauges can be half-bridge-type strain gauges 1204, such as Onyehn 4 pcs 50 kg Human Scale Load Cell Resistance Half-bridge/Amplifier Strain Weight Sensors with 1 pcs HX711 AD Weight Modules for Arduino DIY Electronic Scale strain gauges. In some embodiments, the strain gauges can be S-type strain gauges 1206, such as SENSORTRONICS S-TYPE LOAD CELL 60001 strain gauges. Additionally, the strain gauges can be button-type strain gauges 1208, such as Omega LCGB-250 250 lb Capacity Load Cells. Naturally, the load cells 110 can comprise combinations of these various examples. The embodiments described herein are not limited to these examples.

Figure 10:
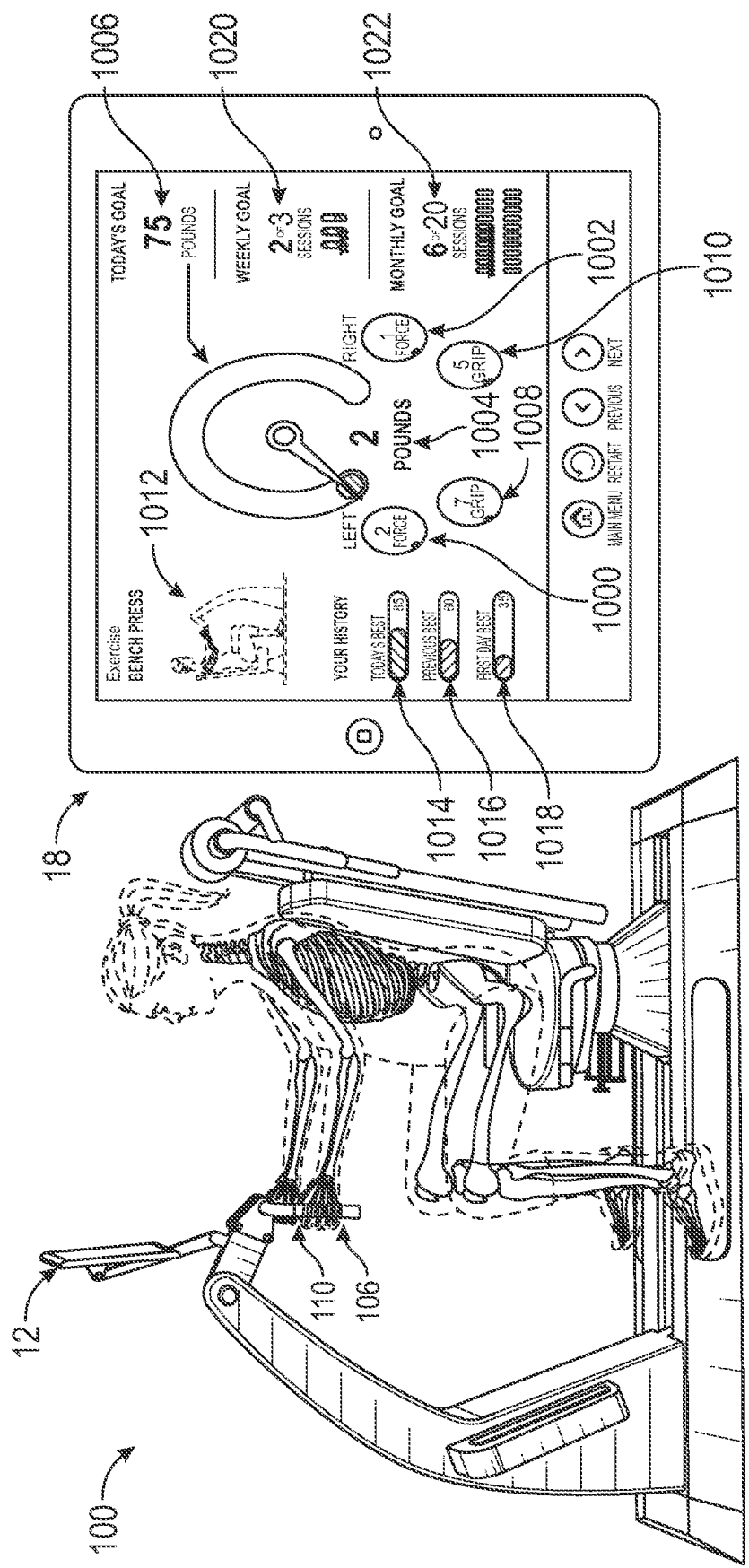
FIG. 10 illustrates a side view of a second embodiment of the isometric exercise and rehabilitation assembly with the user performing a chest-press-style exercise and a user interface presenting information to the user.

FIG. 10-13 illustrate views of a second embodiment of the isometric exercise and rehabilitation assembly 100. FIG. 10 illustrates a side view of the second embodiment of the isometric exercise and rehabilitation assembly 100 with the user performing a chest-press-style exercise and a user interface 18 presenting information to the user. As depicted, the user is the gripping second pair of load handles 106. A left load cell 110 and a right load cell 110 may be located at a left load handle 106 and a right load handle 106, respectively, in the second pair of load handles 106. The user may push on the second pair of load handles 106 to add load to the left load cell 110 and the right load cell 110. The left load cell 110 may transmit a left load measurement to the computing device 102, and the right load cell 110 may transmit a right load measurement to the computing device 102. The computing device 102 may use the load measurements to provide various real-time feedback on the user interface 18 as the user performs the chest-press-style exercise.

In general, the user interface 18 may present real-time visual feedback of the current load measurements or the current forces corresponding to the load measurements, a weight in pounds associated with the load measurements, incentive messages that encourage the user to exceed target thresholds (e.g., to trigger osteogenesis and/or muscular hypertrophy) and/or set personal records for maximum loads, historical performance of the user performing the exercise, and/or scripted prompts that display images of one or more body portions indicating proper technique for performing the exercise. The control system may provide various visual, audio, and/or haptic feedback to encourage the user to exceed their target thresholds.

Initially, when the user has not added load onto any portion of the exercise machine 100 including one or more load cells 110, the computing system 12 may be operating in an idle mode. During the idle mode, the computing system 12 may be receiving load measurements at a first frequency from each data channel associated with an exercise. For example, there may be four data channels, one for each of a chest-press-style exercise, a leg-press-style exercise, a suitcase-lift-style exercise, and a pulldown-style exercise. Although four data channels are described for explanatory purposes, it should be understood that there may be any suitable number of data channels, where "any" refers to one or more. Each data channel may provide load measurements to the computing device 12 from a respective left load cell and a respective right load cell that are located at the portion of the exercise machine 100 where the user pushes or pulls for the respective exercises. The user interface 18 may present the load measurement from each left and right load cells (e.g., 8 load measurements for the 4 data channels associated with the 4 exercises). Further, any target thresholds and/or safety limits for the user performing the exercises may be presented on the user interface 18 during the idle mode. For example, a left target threshold, a right target load threshold, a safety limit, and/or a total weight target threshold for each of the exercises may be presented on the user interface 18 during the idle mode.

If the computing device 12 detects a minimum threshold amount of load (e.g., at least 10 pound-force (lbf)) added onto any of the load cells, the computing device switches from an idle mode to an exercise mode. The data channel including the load cell that sent the detected load measurement may be set to active by the computing device 12. Further, the computing device 12 may set the other data channels to inactive and may stop receiving load measurements from the load cells corresponding to the inactive data channels. The computing device 12 may begin reading data from the load cells at the active data channel at a second frequency higher (e.g., high frequency data collection) than the first frequency when the computing device 12 was operating in the idle mode. Further, the user interface 18 may switch to presenting information pertaining to the exercise associated with the active data channel and stop presenting information pertaining to the exercises associated with the inactive data channels.

For example, the user may grip the second pair of handles 106 and apply force. The computing device 102 may detect the load from the load cells 110 located at the second pair of handles 106 and may set the data channel associated with the chest-press-style exercise to active to begin high frequency data collection from the load cells 110 via the active data channel.

As depicted, the user interface 18 presents a left load measurement 1000 as a left force and a right load measurement 1002 as a right force in real-time or near real-time as the user is pressing on the second pair of handles 106. The values of the forces for the left load measurement 1000 and the right load measurement 1002 are presented. There are separate visual representations for the left load measurement 1000 and the right load measurement 1002. In some embodiments, these load measurements 1000 and 1002 may be represented in a bar char, line chart, graph, or any suitable visual representation. In some embodiments, a left target threshold and a right target threshold for the user may be presented on the user interface 18. In some embodiments, there may be more than one left target threshold and more than one right target threshold. For example, the left target thresholds may relate to an osteopathic therapeutic target threshold determined using a user's disease protocol and/or a muscular strength target threshold determined using a historical performance of the user for a particular exercise. The right target thresholds may relate to an osteopathic therapeutic target threshold determined using a user's disease protocol and/or a muscular strength target threshold determined using a historical performance of the user for a particular exercise. For example, if the user fractured their left arm and is rehabilitating the left arm, but the user's right arm is healthy, the left osteopathic therapeutic target threshold may be different from the right osteopathic therapeutic target threshold.

If the left load measurement 1000 exceeds any of the left target thresholds, an indication (e.g., starburst) may be presented on the user interface 18 indicating that the particular left target threshold has been exceeded and/or osteogenesis and/or muscular hypertrophy has been triggered in one or more portions of the body. If the right load measurement 1002 exceeds any of the right target thresholds, an indication (e.g., starburst) may be presented on the user interface 18 indicating that the particular right target threshold has been exceeded and/or osteogenesis and/or muscular hypertrophy has been triggered in another portion of the body. Further, if either or both of the left and right target thresholds are exceeded, the indication may indicate that the exercise is complete and a congratulatory message may be presented on the user interface 18. In some embodiments, another message may be presented on the user interface 18 that encourages the user to continue adding load to set a new personal maximum left load measurement and/or right load measurement for the exercise.

In some embodiments, there may be a single target threshold to which both the left load measurement and the right load measurement are compared. If either of the left or right load measurement exceed the single target threshold, the above-described indication may be presented on the user interface 18.

In some embodiments, there may be a single safety limit to which the left and right load measurements are compared. The single safety limit may be determined based on the user's disease protocol (e.g., what type of disease the user has, a severity of the disease, an age of the user, the height of the user, the weight of the user, what type of injury the user sustained, what type of surgery the user underwent, the portion of the body affected by the disease, the exercise plan to rehabilitate the user's body, instructions from a caregiver, etc.). If either or both of the left and right load measurements exceed the single safety limit, an indication may be presented on the user interface 18. The indication may warn the user that the safety limit has been exceeded and recommend to reduce the amount of load added to the load cells 110 associated with the exercise being performed by the user.

In some embodiments, more than one safety limit may be used. For example, if the user is rehabilitating a left leg, but a right leg is healthy, there may be a left safety limit that is determined for the left leg based on the user's disease protocol and there may be a right safety limit for the left leg determined based on the user's disease protocol. The left load measurement may be compared to the left safety limit, and the right load measurement may be compared to the right safety limit. If either or both the left load measurement and/or the right load measurement exceed the left safety limit and/or the right safety limit, respectively, an indication may be presented on the user interface 18. The indication may warn the user that the respective safety limit has been exceeded and recommend to reduce the amount of load added to the load cells 110 associated with the exercise being performed by the user.

Further, a total weight 1004 in pounds that is determined based on the left and right load measurements is presented on the user interface 18. The total weight 1004 may dynamically change as the user adds load onto the load cells 110. A target weight 1006 for the exercise for the current day is also presented. This target weight 1006 may be determined based on the user's historical performance for the exercise. If the total weight 1004 exceeds the target weight 1006, an indication (e.g., starburst) may be presented on the user interface 18 indicating that osteogenesis and/or muscular hypertrophy has been triggered. Further, the indication may indicate that the exercise is complete and a congratulatory message may be presented on the user interface 18. In some embodiments, another message may be presented on the user interface 18 that encourages the user to continue adding load to set a new personal maximum record for the exercise.

Additionally, the user interface 18 may present a left grip strength 1008 and a right grip strength 1010. In some embodiments, the left grip strength and the right grip strength may be determined based on the left load measurement and the right load measurement, respectively. Numerical values representing the left grip strength 1008 and the right grip strength 1010 are displayed. Any suitable visual representation may be used to present the grip strengths (e.g., bar chart, line chart, etc.). The grip strengths may only be presented when the user is performing an exercise using handles.

The user interface 18 may also present a prompt 1012 that indicates the body position the user should be in to perform the exercise, as well as indicate which body portions will be targeted by performing the exercise. The user interface 18 may present other current and historical information related to the user performing the particular exercise. For example, the user interface 18 may present a visual representation 1014 of the user's maximum weight lifted, pressed, pulled, or otherwise exerted force for the day or a current exercise session. The user interface 18 may present a visual representation 1016 of the user's previous maximum weight lifted, pressed, pulled, or otherwise exerted force. The user interface 18 may present a visual representation 1018 of the user's maximum weight lifted, pressed, pulled, or otherwise exerted force the first time the user performed the exercise. The user interface 18 may present one or more visual representations 1020 for a weekly goal including how many sessions should be performed in the week and progress of the sessions as they are being performed. The user interface 18 may present a monthly goal including how many sessions should be performed in the month and progress of the sessions as they are being performed. Additional information and/or indications (e.g., incentivizing messages, recommendations, warnings, congratulatory messages, etc.) may be presented on the user interface 18, as discussed further below.

FIG. 11 illustrates a side view of the second embodiment of the isometric exercise and rehabilitation assembly 100 with a user performing a suitcase-lift-style exercise and the user interface 18 presenting information to the user. The user interface 18 may present similar types of information as discussed above with regards to FIG. 10, but the information in the user interface 18 in FIG. 11 may be tailored for the suit-case-lift-style exercise. That is, the data channel for the suitcase-lift-style exercise may be set to active when the computing device 12 detects load measurements from load cells corresponding to the suitcase-lift-style exercise, and the computing device 12 may present the various visual representations described with regards to FIG. 10 on the user interface 18 in FIG. 11 based on at least the load measurements for the suitcase-lift-style exercise.

Figure 12:
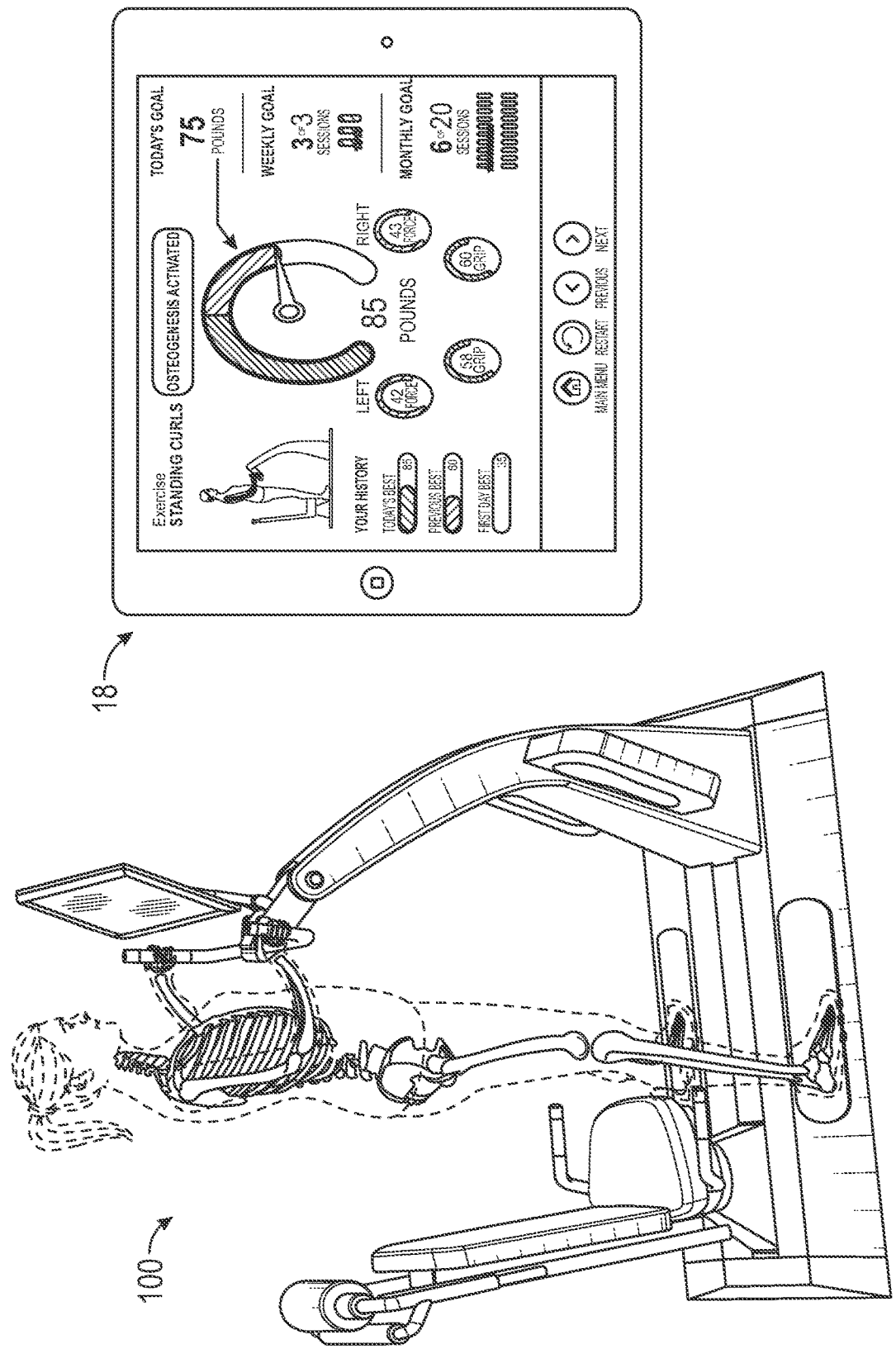
FIG. 12 illustrates a side view of the second embodiment of the isometric exercise and rehabilitation assembly with a user performing an arm-curl-style exercise and a user interface presenting information to the user.

FIG. 12 illustrates a side view of the second embodiment of the isometric exercise and rehabilitation assembly 100 with a user performing an arm-curl-style exercise and a user interface presenting information to the user. The user interface 18 may present similar types information as discussed above with regards to FIG. 10, but the information in the user interface 18 in FIG. 12 may be tailored for the arm-curl-style exercise. That is, the data channel for the arm-curl-style exercise may be set to active when the computing device 12 detects load measurements from load cells corresponding to the arm-curl-style exercise, and the computing device 12 may present the various visual representations described with regards to FIG. 10 on the user interface 18 in FIG. 12 based on at least the load measurements for the arm-curl-style exercise.

FIG. 13 illustrates a side view of the second embodiment of the isometric exercise and rehabilitation assembly 100 with a user performing a leg-press-style exercise and a user interface presenting information to the user. The user interface 18 may present similar types information as discussed above with regards to FIG. 10, but the information in the user interface 18 in FIG. 13 may be tailored for the leg-press-style exercise. That is, the data channel for the leg-press-style exercise may be set to active when the computing device 12 detects load measurements from load cells corresponding to the leg-press-style exercise, and the computing device 12 may present the various visual representations described with regards to FIG. 10 on the user interface 18 in FIG. 13 based on at least the load measurements for the leg-press-style exercise.

Figure 14:
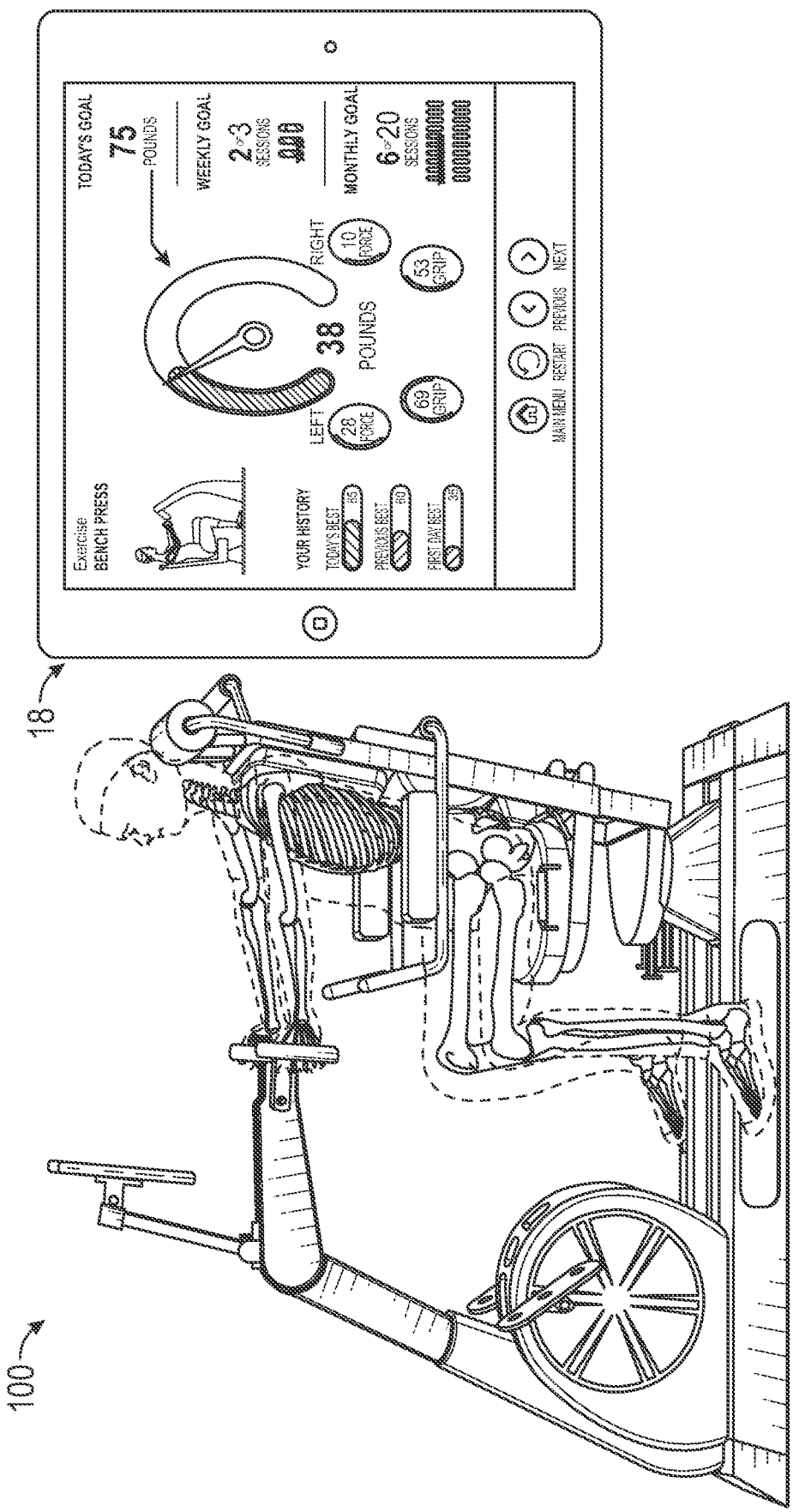
FIG. 14 illustrates a side view of a third embodiment of the isometric exercise and rehabilitation assembly with the user performing a chest-press-style exercise and a user interface presenting information to the user.

FIGS. 14-18 illustrate views of a third embodiment of the isometric exercise and rehabilitation assembly 100. FIG. 14 illustrates a side view of the third embodiment of the isometric exercise and rehabilitation assembly 100 with the user performing a chest-press-style exercise and a user interface 18 presenting information to the user. The user interface 18 in FIG. 14 may present similar types of information as discussed above with regards to FIG. 10.

FIG. 15 illustrates a side view of the third embodiment of the isometric exercise and rehabilitation assembly 100 with the user performing a pull-down-style exercise and a user interface 18 presenting information to the user. The user interface 18 may present similar types of information as discussed above with regards to FIG. 10, but the information in the user interface 18 in FIG. 15 may be tailored for the pull-down-style exercise. That is, the data channel for the pull-down-style exercise may be set to active when the computing device 12 detects load measurements from load cells corresponding to the pull-down-style exercise, and the computing device 12 may present the various visual representations described with regards to FIG. 10 on the user interface 18 in FIG. 15 based on at least the load measurements for the pull-down-style exercise.

FIG. 16 illustrates a side view of the third embodiment of the isometric exercise and rehabilitation assembly with a user performing an arm-curl-style exercise and a user interface 18 presenting information to the user. The user interface 18 may present similar types of information as discussed above with regards to FIG. 12.

Figure 17:
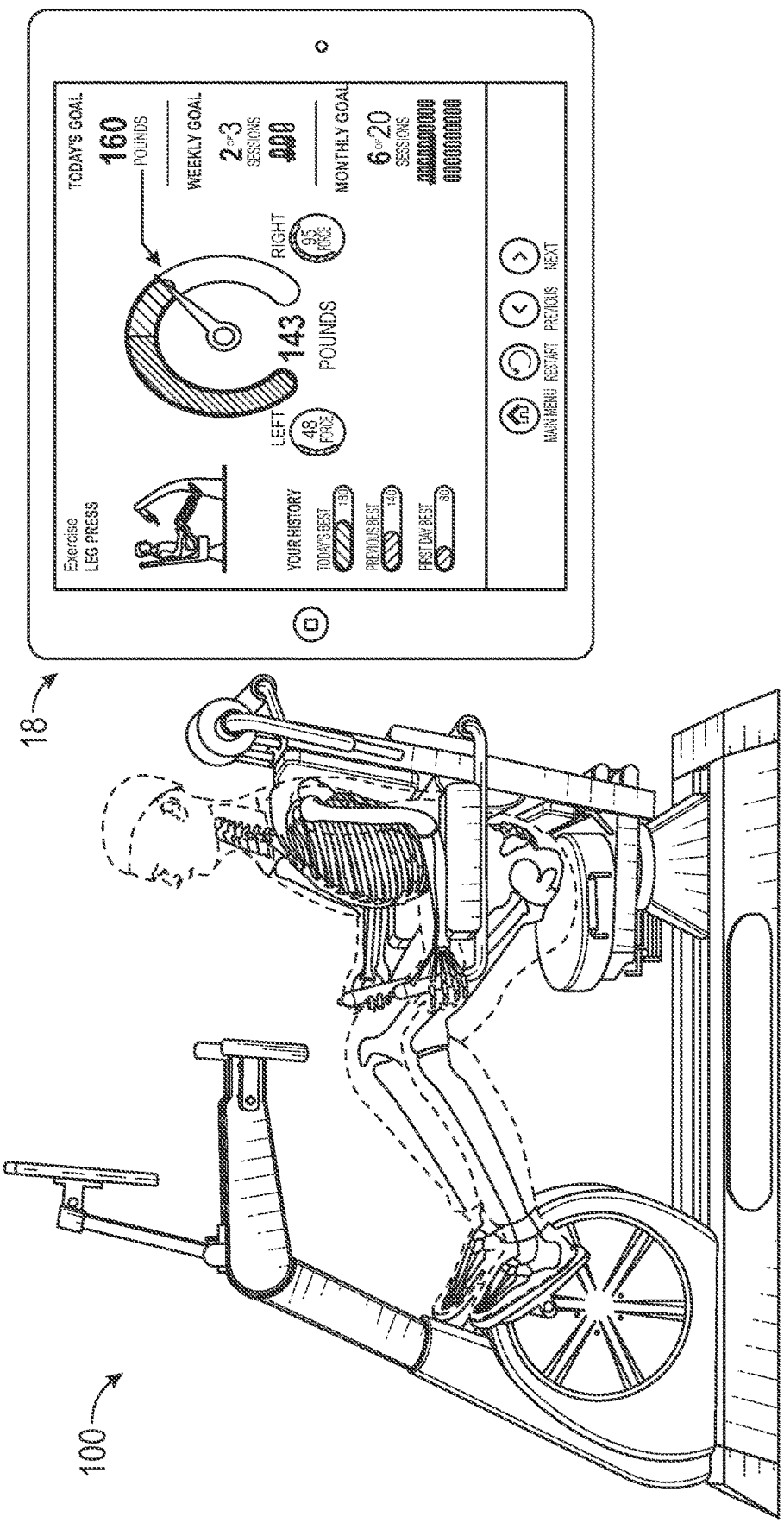
FIG. 17 illustrates a side view of the third embodiment of the isometric exercise and rehabilitation assembly with a user performing a leg-press-style exercise and a user interface presenting information to the user.

FIG. 17 illustrates a side view of the third embodiment of the isometric exercise and rehabilitation assembly 100 with a user performing a leg-press-style exercise and a user interface 18 presenting information to the user. The user interface 18 may present similar types of information as discussed above with regards to FIG. 13.

FIG. 18 illustrates a side view of the third embodiment of the isometric exercise and rehabilitation assembly 100 with a user performing a suitcase-lift-style exercise and a user interface 18 presenting information to the user. The user interface 18 may present similar types of information as discussed above with regards to FIG. 11.

Figure 19A:
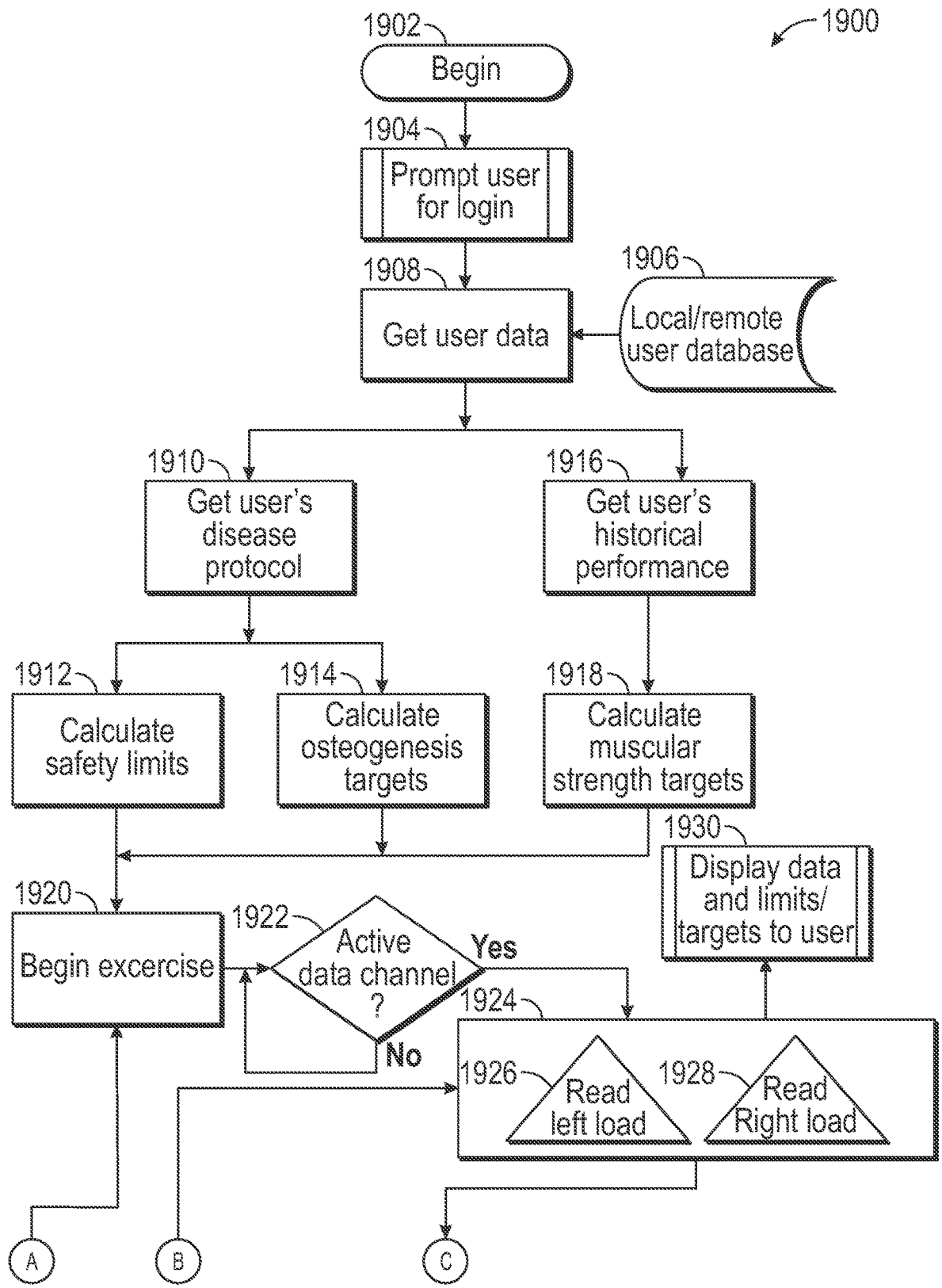
FIGS. 19A and 19B illustrate example operations of a method for improving compliance with an exercise.
Figure 19B:
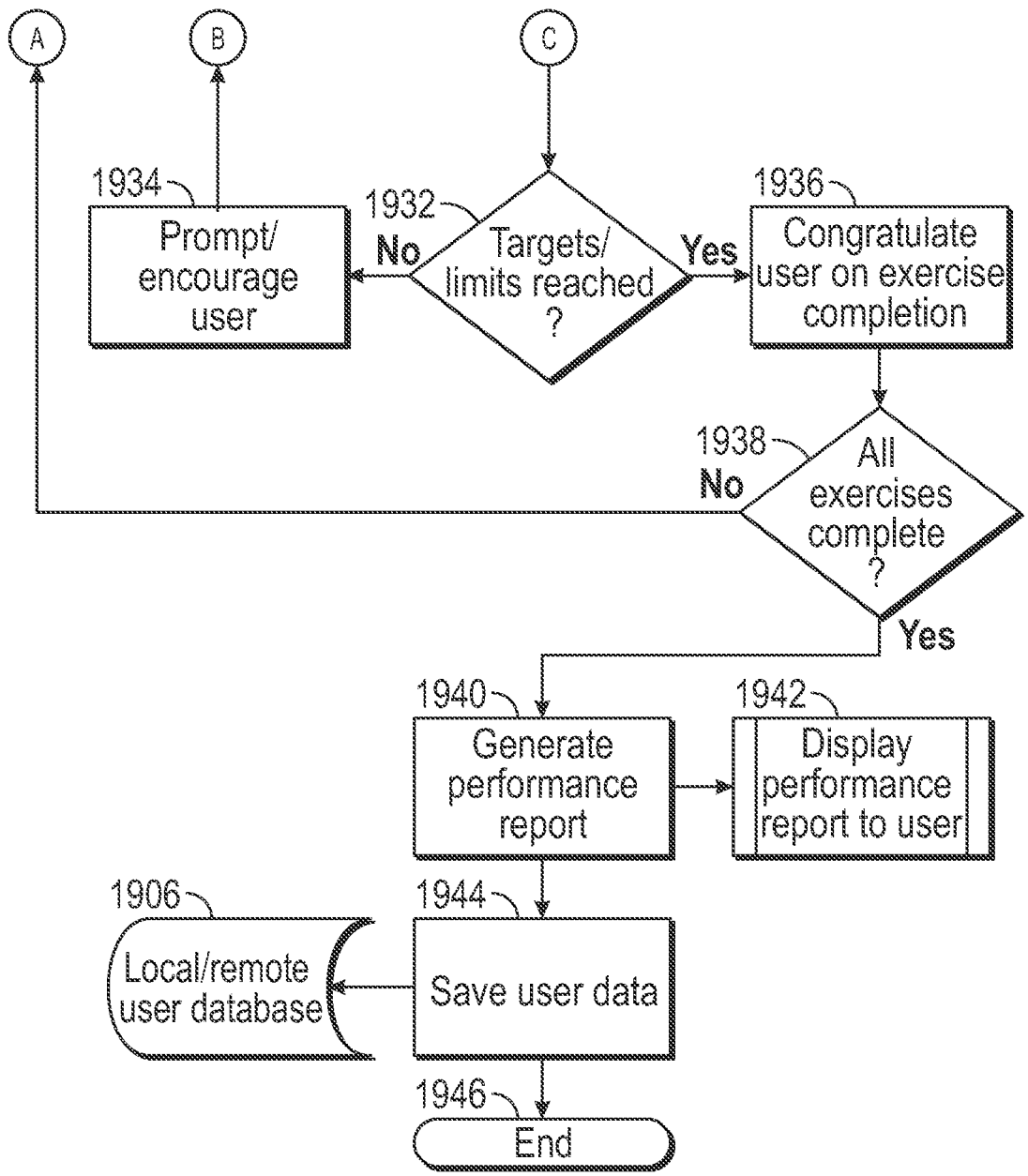

FIGS. 19A and 19B illustrate example operations of a method 1900 for improving compliance with an exercise.

The method 1900 may be performed by processing logic that may include hardware (circuitry, dedicated logic, etc.), firmware, software, or a combination of them. The method 1900 and/or each of their individual functions, subroutines, or operations may be performed by one or more processing devices of a control system (e.g., computing device 12 of FIG. 1) implementing the method 1900. The method 1900 may be implemented as computer instructions that are executable by a processing device of the control system. In certain implementations, the method 1900 may be performed by a single processing thread. Alternatively, the method 1900 may be performed by two or more processing threads, each thread implementing one or more individual functions, routines, subroutines, or operations of the methods. Various operations of the method 1900 may be performed by one or more of the cloud-based computing system 16, and/or the computing device 15 of FIG. 1.

The method may begin at 1902. At 1904, the processing device may prompt the user for login on the user interface 18. The user may input their credentials (e.g., username and password) via an input device (e.g., mouse, keyboard, touchscreen) of the computing device 12. The processing device may compare the credentials to stored credentials in a local and/or remote database 1906. The database 1906 may be locally stored on the computing device 12, remotely stored on the computing device 15, or remotely stored on the cloud-based computing system 16. If the processing device validates the credentials for a user, then the processing device may obtain a user identifier associated with the credentials. At 1908, the processing device may obtain user data based on the user identifier. The user data may include personal information about the user (e.g., name, height, weight, age, gender, address, contact information, exercise plan, etc.).

At 1910, the processing device may obtain the user's disease protocol. At 1912, the processing device may calculate one or more safety limits using the user's disease protocol. There may be different safety limits calculated for different exercises. Further, there may be different left and right safety limits calculated for each exercise. The safety limits may be an upper limit of an amount of load or force that is determined to be acceptable for the user based on the disease protocol. The safety limit calculation may consider one or more factors, such as a portion of the body exercised by the exercise, an age of the user, a height of the user, a weight of the user, a gender of the user, a type of injury that occurred to the user at or near the portion of the body being exercised, a severity of the type of injury, a type of disease affecting the portion of the body, a severity of the type of disease affecting the portion of the body, a surgery performed on the user at or near the portion of the body, and so forth.

At 1914, the processing device may calculate one or more osteopathic therapeutic target thresholds using the user's disease protocol. There may be different osteopathic therapeutic target thresholds calculated for different exercises. Further, there may be different left and right osteopathic therapeutic target thresholds calculated for each exercise for the user. The osteopathic therapeutic target thresholds may be an amount of load or force, determined for the user, that, when exceeded, trigger osteogenesis in the portion of the body of the user targeted by the respective exercise. The osteopathic therapeutic target threshold calculation may consider one or more factors, such as a portion of the body exercised by the exercise, an age of the user, a height of the user, a weight of the user, a gender of the user, a type of injury that occurred to the user at or near the portion of the body being exercised, a severity of the injury, a type of disease affecting the portion of the body, a severity of the type of disease affecting the portion of the body, a medical procedure performed on the user at or near the portion of the body, and so forth.

At 1916, the processing device may obtain the user's historical performance for the exercises available at the exercise machine 100. For example, the processing device may have stored the user's past load measurements that were obtained from the load cells associated with each exercise as the user performed the exercises in an exercise plan. At 1918, the processing device may calculate muscular strength target thresholds for the user using the user's historical performance. There may be different muscular strength target thresholds calculated for different exercises. Further, there may be different left and right muscular strength target thresholds calculated for each exercise for the user. In some embodiments, the processing device may determine an average amount of load the user added to the load cells over time and may set a muscular strength target to an amount of load that is the same as or higher than the average amount of load by a certain percent to encourage the user to maintain or increase muscle mass. In some embodiments, the processing device may determine a maximum amount of load the user added to the load cells in the past and may set a muscular strength target to an amount of load that is the same as or higher than the maximum amount to maintain or increase muscle mass.

At 1920, the user may begin the exercise by adding a load to one or more load cells located at handles or feet of the exercise machine 100. The one or more load cells may transmit load measurements to the processing device. At 1922, the processing device may determine whether a minimum threshold amount of load is detected. If so, the processing device may switch from the idle mode to the exercise mode, and may set a data channel associated with the load cells that transmitted the minimum threshold amount of load to active and set the other data channels associated with other exercises to inactive. If there is not a minimum threshold amount of load detected via any of the load cells via the data channels associated with the exercises, the processing device may continue to monitor for the minimum threshold amount of load.

When there is an active data channel, at 1924, the processing device may begin reading a left load cell (1926) and a right load cell (1928) at a higher frequency than when the processing device was operating in the idle mode. At 1930, the processing device may present, on the user interface 18, one or more received load measurements from the left and right load cells in real-time, along with the one or more target thresholds (e.g., one or more osteopathic therapeutic target thresholds, and/or one or more muscular strength target thresholds) determined for the user for the exercise and the one or more safety limits determined for the user for the exercise.

At 1932, the processing device may determine whether the one or more received load measurements exceed the one or more target thresholds and/or the one or more safety limits. If the one or more target thresholds are not exceeded, then at 1934, the processing device may present, on the user interface 18, a prompt or encouraging message that instructs the user to add additional load to the load cells to exceed the one or more target thresholds and complete the exercise. If the one or more target thresholds are exceeded, then at 1936, the processing device causes an indication to be presented on the user interface 18 that indicates the exercise is complete, congratulates the user for completing the exercise, and/or encourages the user to add additional load to the load cells to achieve a new maximum record.

At 1938, the processing device determines if all exercises are complete. If there are any incomplete exercises in the exercise plan for the user, the user interface 18 may present a prompt to the user to begin an incomplete exercise in the exercise plan. The processing device may transition back to 1920 if the user begins an incomplete exercise.

After a threshold period of time after an exercise is completed, the processing device may switch back to the idle mode to monitor for the minimum threshold amount of load from load cells associated with an incomplete exercise in the exercise plan. If load is detected from load cells associated with an exercise that has already been completed, the user interface 18 may present an indication notifying the user that that particular exercise has already been completed and to begin an incomplete exercise. The indication may present a list of the complete exercises and the incomplete exercises to enable the user to track their progress in the exercise plan.

If all exercises in the exercise plan are complete, the indication may congratulate the user for completing the exercise plan. At 1940, the processing device may generate a performance report that may include data pertinent to the exercise plan just completed and/or to exercise plans that were completed in the past. The performance report may include any suitable graphs, charts, and/or summaries. For example, the performance report may include a percent gain in load over time for each exercise based on the current data and the historical data for each exercise. The performance report may include the maximum loads added by the user for the left and right load measurements for each exercise, and/or the maximum weights determined based on the load measurements for each exercise. The performance report may include the target thresholds and/or safety limits that were exceeded. At 1942, the processing device may present the performance report to the user. At 1944, the processing device may save the data received while the user was performing the exercises and/or generated for the performance report to the database 1906. At 1946, the method 1900 ends.

FIG. 20 illustrates example operations of another method 2000 for improving compliance with an exercise. Method 2000 includes operations performed by processing devices of the control system (e.g., computing device 12) of FIG. 1. In some embodiments, one or more operations of the method 2000 are implemented in computer instructions that are executable by a processing device of the control system. Various operations of the method 2000 may be performed by one or more of the computing device 15 and/or the cloud-based computing system 16. The method 2000 may be performed in the same or a similar manner as described above in regards to method 1900.

At 2002, the processing device may receive one or more load measurements from one or more load cells 110 of the exercise machine 100. The exercise machine 100 may be a machine enabling osteogenesis, a machine enabling muscular hypertrophy, or some combination thereof. The one or more load measurements may be received from one or more load cells 110 in a left handle of the exercise machine 100, in a right handle of the exercise machine 100, in a left foot plate of the exercise machine 100, in a right foot plate of the exercise machine 100, or some combination thereof.

The load cells 110 may be associated with a data channel for a particular exercise. For example, for a leg-press-style exercise, there may be one or more load cells 110 located at a left foot plate and one or more load cells 110 located at a right foot plate. When one or more load measurements are detected for load cells 110 associated with a data channel, the processing device may switch from an idle mode to an exercise mode and set that data channel to active. The processing device may begin exclusively reading load measurements from the active data channel at a higher frequency than when operating in the idle mode. The processing device may stop reading load measurements from the other data channels associated with other exercises. In some embodiments, receiving the one or more load measurements from the one or more load cells 110 of the exercise machine 100 may include receiving a left load measurement from a left load cell 110 of the exercise machine 100 and receiving a right load measurement from a right load cell 110 of the exercise machine 100.

At 2004, the processing device may compare the one or more load measurements to one or more target thresholds. As discussed above, the one or more target thresholds may include at least one osteopathic therapeutic target threshold and at least one muscular strength target threshold. The at least one osteopathic therapeutic target threshold may be determined based on health information pertaining to a user using the exercise machine. For example, the health information may be a disease protocol for the user. The at least one muscular strength target threshold may be determined based on at least one historical performance pertaining to the user previously using the exercise machine. For example, the at least one historical performance may include a maximum weight that the user lifted, pressed, pulled, or otherwise exerted force from the last time the user performed the same exercise. There may be different osteopathic therapeutic target thresholds for the left side of the user's body and the right side of the user's body (e.g., when the user is rehabilitating a left knee and not the right knee). Further, there may be different muscular strength target thresholds for the left side of the user's body and the right side of the user's body (e.g., when the user is rehabilitating the left knee and not the right knee). Accordingly, comparing the one or more load measurements to the one or more target thresholds may include comparing a left load measurement to a left target threshold (e.g., osteopathic therapeutic target threshold and/or muscular strength target threshold) and comparing a right load measurement to a right target threshold (e.g., osteopathic therapeutic target threshold and/or muscular strength target threshold). In some embodiments, the left load measurement may be compared to a right target threshold and/or the right load measurement may be compared to a left target threshold.

At 2006, the processing device may determine whether the one or more load measurements exceed the one or more target thresholds. Exceeding the osteopathic therapeutic target threshold determined for the user may indicate that osteogenesis has been triggered. Further, exceeding the muscular strength target threshold determined for the user may indicate that muscular hypertrophy has been triggered.

In some embodiments, the processing device may cause a user interface 18 to present a visual representation of the left load measurement concurrently with another visual representation of the right load measurement. For example, each load measurement may be represented as a respective bar in a bar chart, a line in a line chart, or any suitable visual representation. Presenting each load measurement as its own visual representation may enable the user to visualize the amount of load they are adding on the left and right side of the exercise machine 100.

At 2008, responsive to determining that the one or more load measurements satisfy the one or more target thresholds, the processing device may cause a user interface 18 to present an indication that the one or more target thresholds have been satisfied and an exercise is complete. The exercise may be included in an exercise plan for the user. The processing device may cause a congratulatory message to be presented on the user interface 18. The processing device may cause an indication to be presented on the user interface 18 that instructs the user to continue to add load to attempt to set a new personal maximum weight lifted, pressed, pulled, or otherwise exert force for the exercise.

Responsive to determining that the exercise in the exercise plan is complete, the processing device may determine whether another exercise in the exercise plan is incomplete. Responsive to determining that the another exercise in the exercise plan is incomplete, the processing device may cause the user interface 18 to present an indication to begin the another exercise. In some embodiments, responsive to determining that all exercises in the exercise plan are complete, the processing device may cause the user interface 18 to present an indication that all exercises in the exercise plan are complete. The processing device may cause a congratulatory message to be presented on the user interface 18 that congratulates the user for completing the exercise plan for a session.

In some embodiments, while the user is applying force to the one or more load cells associated with an exercise, the processing device may determine whether the one or more load measurements are less than the one or more target thresholds. Responsive to determining that the one or more load measurements are less than the one or more target thresholds, the processing device may cause the user interface 18 to present an indication to recommend an addition of one or more loads onto the one or more load cells 110 to exceed the one or more target thresholds. Providing these indications to encourage the user may enhance compliance with the exercise by motivating the user to exceed the target thresholds, thereby potentially triggering osteogenesis and/or muscular hypertrophy.

In some embodiments, the processing device may compare the one or more load measurements to one or more safety limits. The one or more safety limits may be determined based on the health information pertaining to the user using the exercise machine 100. For example, a disease protocol may be used to determine what a safe amount of load for the user to apply for each particular exercise. There may be different safety limits for the left side of the user's body and the right side of the user's body. For example, a left safety limit for a left leg of the user that is being rehabilitated after knee surgery may be 50 pounds, while a right safety limit for a right leg that did not undergo knee surgery may be 100 pounds for a leg-press-style exercise. Accordingly, the processing device may compare the left load measurement to a left safety limit and the right load measurement to a right safety limit. In some embodiments, there may be a single safety limit determined for each exercise or for all of the exercises.

The processing device may determine whether the one or more load measurements exceed the one or more safety limits. Responsive to determining that the one or more load measurements exceed the one or more safety limits, the processing device may provide an alert to indicate that the one or more safety limits are exceeded. The alert may include at least one of a visual indication on the user interface 18, an auditory indication via a speaker, or a haptic feedback. The alert may be provided via at least one of a handle, a foot platform or plate, a seat of the exercise machine 100, a backboard of the exercise machine 100, or some combination thereof.

FIG. 21 illustrates example operations of another method 2100 for improving compliance with an exercise. Method 2100 includes operations performed by processing devices of the control system (e.g., computing device 12) of FIG. 1. In some embodiments, one or more operations of the method 2100 are implemented in computer instructions that are executable by a processing device of the control system. Various operations of the method 2100 may be performed by one or more of the computing device 15 and/or the cloud-based computing system 16. The method 2100 may be performed in the same or a similar manner as described above in regards to method 1900.

At 2102, the processing device may receive one or more load measurements obtained from one or more load cells 110 included in the exercise machine 100. The one or more load cells 110 may be located in a left handle, a right handle, a left foot plate, a right foot plate, or some combination thereof. The one or more load cells 110 may be associated with a data channel for a particular exercise. In some embodiments, the one or more load measurements includes a right load measurement and a left load measurement.

At 2104, the processing device may present one or more visual representations for the one or more load measurements in a user interface 18 on a display screen of a computing device 12. For example, a visual representation for the right load measurement may be presented on the user interface 18 concurrently with another visual representation (e.g., a value of the amount of load, a bar in a bar chart, a line in a line chart, etc.) for the left load measurement. Independent visual representations for each of the left and right load measurement may enable the user to track how much load they are adding on both the left and right side of the exercise machine 100 during the exercise. Further, various target thresholds may be presented concurrently with the visual representations of the left and right load measurements. For example, an osteopathic therapeutic target threshold and/or a muscular strength target threshold may be presented at the same time as the visual representations of the left and right load measurements. In this way, the user may compare the current left and right load measurements to the target thresholds in real-time to determine how close they are to exceeding the target thresholds and when the target thresholds are exceeded.

At 2106, the processing device may receive an indication that an exercise in the exercise plan is complete based on the one or more load measurements having satisfied one or more target thresholds. At 2108, the processing device may present, with the one or more visual representations, the indication in the user interface 18 that the exercise is complete. The processing device may present a congratulatory message with the indication that the exercise is complete. In some embodiments, the processing device may encourage the user to add additional load to the one or more load cells to attempt to set a new personal maximum weight lifted, pressed, pulled, or otherwise exert force for that exercise. If the user sets a new personal maximum weight lifted, pressed, pulled, or otherwise exerted force for that exercise, the processing device may present another indication on the user interface 18 that the new personal maximum weight has been set and congratulate the user.

In some embodiments, prior to the one or more load measurements exceeding the one or more target thresholds, the processing device may receive a second indication that the exercise is almost complete based on the one or more load measurements being less than the one or more target thresholds. The processing device may present, with the one or more visual representations in the user interface 18 on the display screen, the second indication that the exercise is almost complete and to continue adding one or more loads onto the one or more load cells 110 of the exercise machine 100.

After the exercise is complete, the processing device may receive another indication to complete another exercise in the exercise plan based on the control system determining that the another exercise is incomplete. The processing device may present, in the user interface 18, the second indication to complete the another exercise in the exercise plan.

In some embodiments, while the user is performing the exercise, the processing device may receive an alert that the one or more load measurements have exceeded one or more safety limits. The processing device may present, in the user interface 18 on the display screen, the alert that the one or more load measurements have exceeded the one or more safety limits. Further, the processing device may present a message that instructs the user to reduce the amount of load they are currently adding onto the load cells 110.

Figure 22:
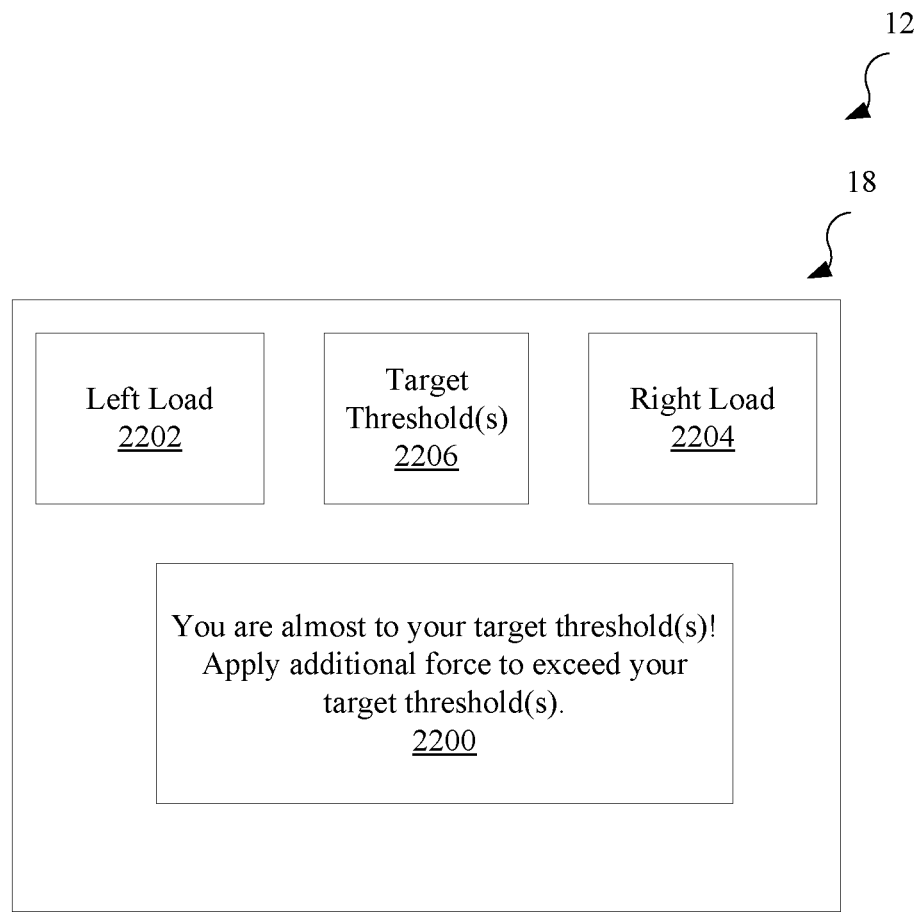
FIG. 22 illustrates an example user interface presenting a recommendation to apply additional force to reach a target.

FIG. 22 illustrates an example user interface 18 presenting a recommendation 2200 to apply additional force to reach a target threshold. The user interface 18 may be presented on a display screen of the computing device 12. The user interface 18 may also present a visual representation 2202 for a left load measurement or force measurement and a visual representation 2204 for a right load measurement or force measurement. In some embodiments, the visual representations 2202 and/or 2204 may be numerical values of the respective load measurements. In some embodiments, the visual representation 2202 and/or 2204 may be bars on a bar chart, lines on a line chart, or any suitable visual representation.

Further, the user interface 18 may present one or more visual representations 2206 of target thresholds that are tailored for the user. For example, the one or more target thresholds may include a left osteopathic therapeutic target threshold, a right osteopathic therapeutic target threshold, a left muscular strength target threshold, a right muscular strength target threshold, a total target weight to be lifted, pressed, pulled, or otherwise exert force for the current exercise, or some combination thereof. Presenting the visual representations 2206 of the target thresholds concurrently with the real-time display of the load measurements in the visual representations 2202 and/or 2204 may enable the user to determine how close they are to exceeding the target thresholds and/or when they exceed the target thresholds.

In the current example in FIG. 22, the control system determined that the one or more load measurements are less than the one or more target thresholds. As such, the example recommendation 2200 indicates that "You are almost to your target threshold(s)! Apply additional force to reach your target." The recommendation may be more specific and recommend applying more force to a specific portion (e.g., left foot plate, right foot plate, left handle, and/or right handle) of the exercise machine 100 to exceed the one or more target thresholds.

Figure 23:
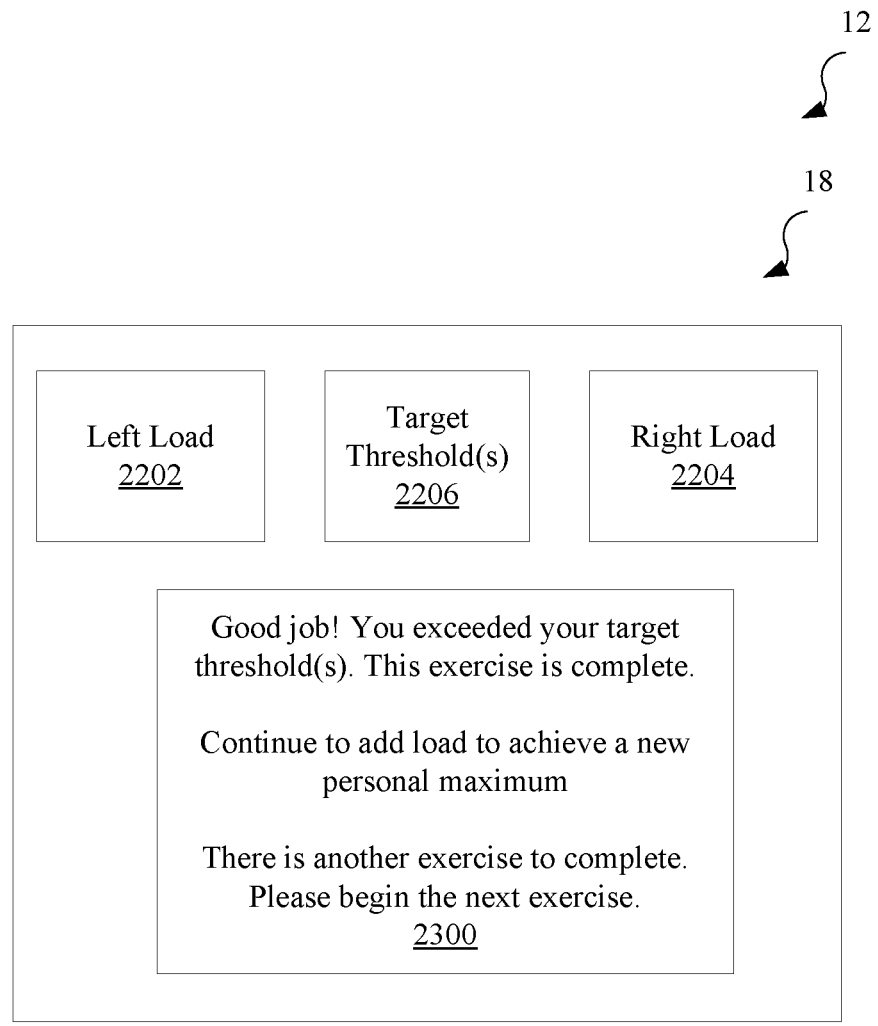
FIG. 23 illustrates an example user interface presenting an indication that an exercise is complete and congratulates the user.

FIG. 23 illustrates an example user interface 18 presenting an indication 2300 that an exercise is complete and congratulates the user. Further, the indication 2300 instructs the user to continue adding load to try to set a new personal maximum weight lifted, pressed, pulled, or otherwise exert force for the particular exercise. The indication 2300 indicates there is another exercise in the exercise plan to complete and instructs the user to begin performing the next exercise. For example, the indication 2300 states "Good job! You exceeded your target threshold(s). This exercise is complete. Continue to add load to achieve a new personal maximum. There is another exercise to complete. Please begin the next exercise." Automatic encouraging and guiding the user to complete the next exercise may improve completion of exercises in an exercise plan.

The user interface 18 in FIG. 23 may present the visual representations 2202 and/or 2204 for the left and right load measurements, respectively, as described with reference to FIG. 22. Further, the user interface 18 in FIG. 23 may also present the visual representation 2206 for the one or more target thresholds, as described with reference to FIG. 22.

Figure 24:
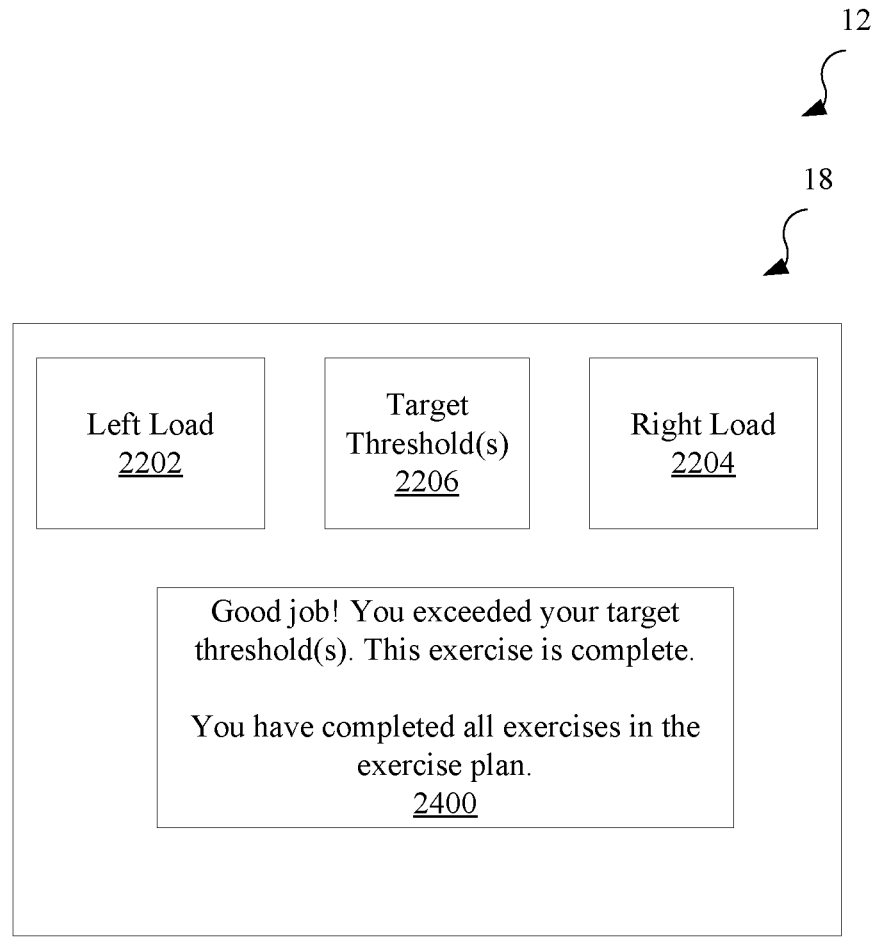
FIG. 24 illustrates an example user interface presenting an indication that all exercises in the exercise plan are complete.

FIG. 24 illustrates an example user interface 18 presenting an indication 2400 that all exercises in the exercise plan are complete. Upon the one or more load measurements exceeding the one or more target thresholds, the processing device may determine whether there are any exercises in the exercise plan that are incomplete. If all exercises in the exercise plan are complete, the indication 2400 may congratulate the user and inform the user that the exercise plan is complete. The indication 2400 may say "Good job! You exceeded your target thresholds(s). This exercise is complete. You have completed all exercises in the exercise plan."

The user interface 18 in FIG. 24 may present the visual representations 2202 and/or 2204 for the left and right load measurements, respectively, as described with reference to FIG. 22. Further, the user interface 18 in FIG. 24 may also present the visual representation 2206 for the one or more target thresholds, as described with reference to FIG. 22.

Figure 25:
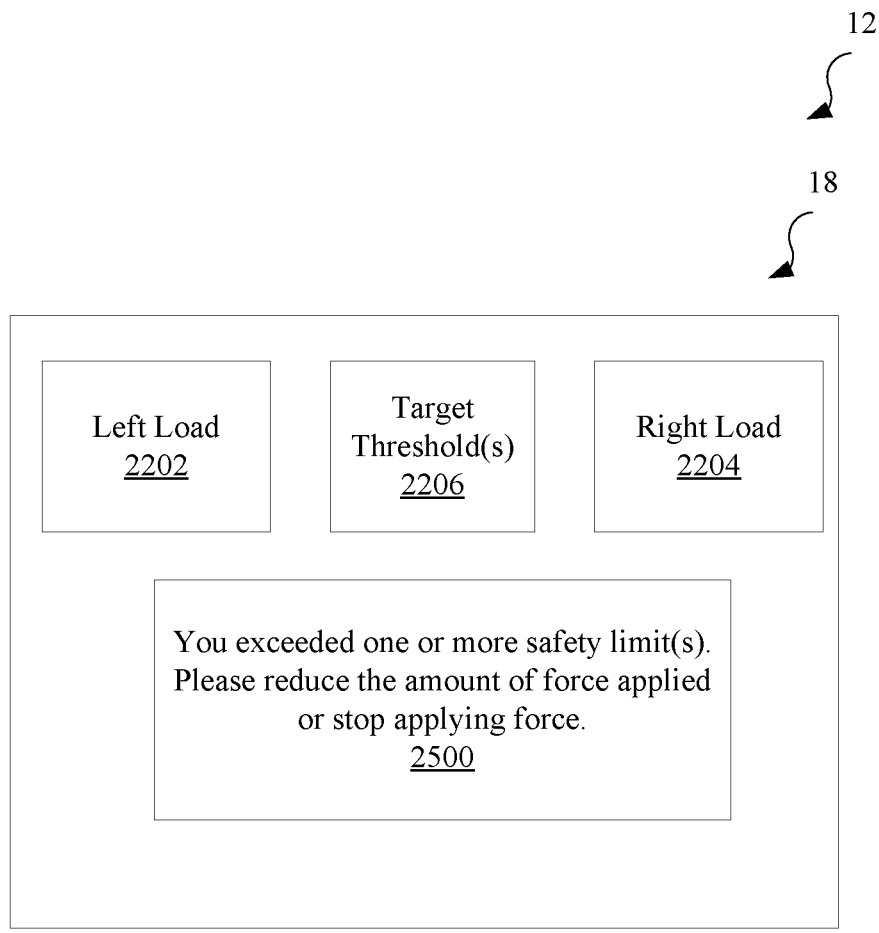
FIG. 25 illustrates an example user interface presenting an indication that a safety limit is exceeded.

FIG. 25 illustrates an example user interface 18 presenting an indication 2500 that a safety limit is exceeded. The safety limit may be determined for a user based on health information pertaining to the user. For example, a disease protocol pertaining to a user's disease (e.g., muscular dystrophy) may be used to set a safety limit for the user. The processing device may determine when one or more of the load measurements exceed one or more safety limits by comparing the one or more load measurements to the one or more safety limits. The indication 2500 may recommend that the user reduce an amount of applied force and/or stop applying force altogether. The indication 2500 may vary depending on how much the user has exceeded the one or more safety limits. The indication 2500 may say "You exceeded one or more safety limits. Please reduce the amount of force applied or stop applying force."

The user interface 18 in FIG. 25 may present the visual representations 2202 and/or 2204 for the left and right load measurements, respectively, as described with reference to FIG. 22. Further, the user interface 18 in FIG. 25 may also present the visual representation 2206 for the one or more target thresholds, as described with reference to FIG. 22.

Figure 26:
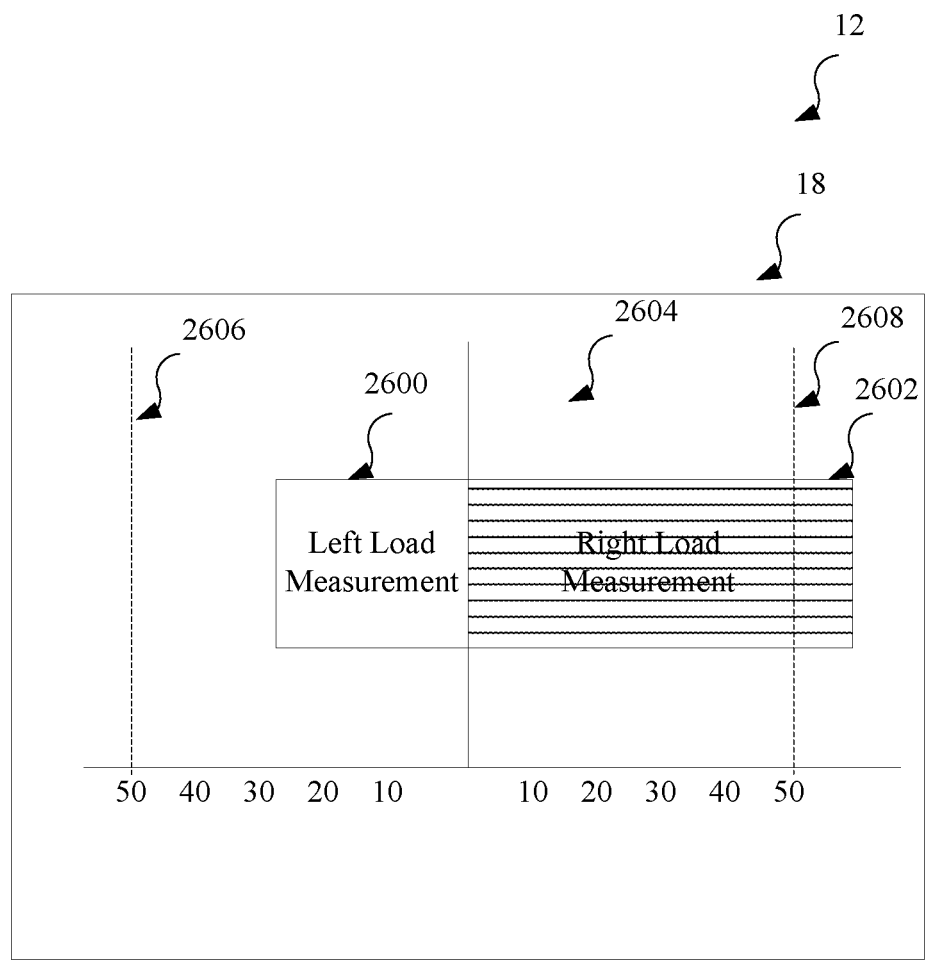
FIG. 26 illustrates an example user interface presenting separate visual representations for a left load measurement and a right load measurement in a bar chart.

FIG. 26 illustrates an example user interface 18 presenting a visual representation 2600 for a left load measurement and a visual representation 2602 for a right load measurement in a bar chart 2604. As depicted, each visual representation 2600 and 2602 are separate bars in the bar chart 2604. The bar chart 2604 includes values for the amount of loads along the x-axis. The visual representations 2600 and 2602 protrude from the y-axis in opposite directions. The example bar chart 2604 may enable a user to visualize how much load they are adding on a left side and right side of the exercise machine 100 in real-time. In some embodiments, if there are multiple load cells at a portion of the machine (e.g., left foot plate), there may be multiple bars representing the multiple load measurements on a side (e.g., left) of the bar chart 2604. In addition, a left target threshold 2606 may be presented on the bar chart 2604 and a right target threshold 2608 may be presented on the bar chart 2604 to enable a user to visualize how much force to apply to exceed the target thresholds 2606 and 2608 and when the target thresholds 2606 and 2608 are exceeded.

Figure 27:
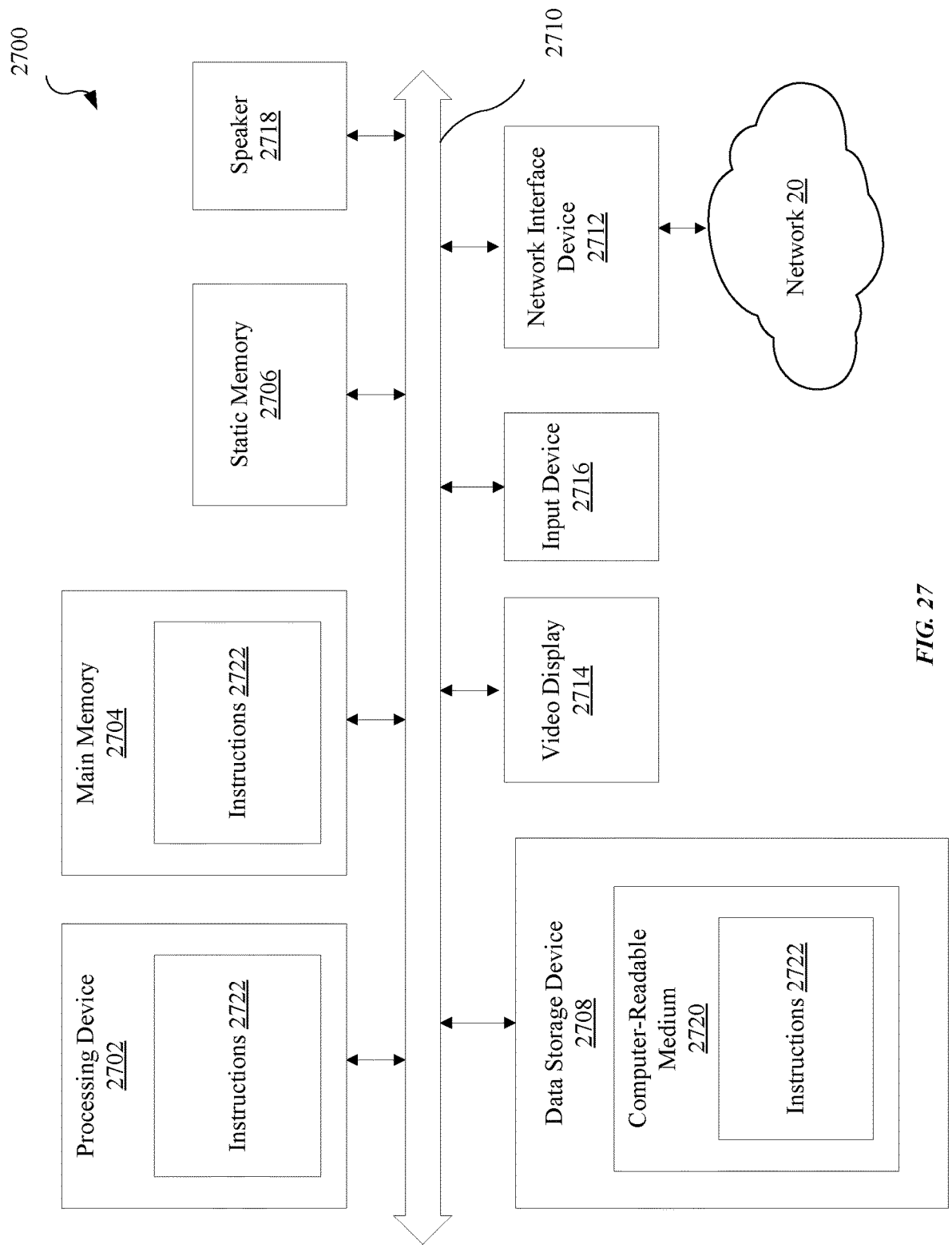
FIG. 27 illustrates an example computer system.

FIG. 27 illustrates an example computer system 2700, which can perform any one or more of the methods described herein. In one example, computer system 2700 may correspond to the computing device 12 (e.g., control system), the computing device 14, one or more servers 28 of the cloud-based computing system 16 of FIG. 1. The computer system 2700 may be capable of the application 17 and presenting the user interface 18 of FIG. 1, and/or the application 21 and presenting the user interface 22 of FIG. 1. The computer system 2700 may be connected (e.g., networked) to other computer systems in a LAN, an intranet, an extranet, or the Internet. The computer system 2700 may operate in the capacity of a server in a client-server network environment. The computer system 2700 may be a personal computer (PC), a tablet computer, a motor controller, a goniometer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 2700 includes a processing device 2702, a main memory 2704 (e.g., read-only memory (ROM), flash memory, dynamic random access memory (DRAM) such as synchronous DRAM (SDRAM)), a static memory 2706 (e.g., flash memory, static random access memory (SRAM)), and a data storage device 2708, which communicate with each other via a bus 2710.

Processing device 2702 represents one or more general-purpose processing devices such as a microprocessor, central processing unit, or the like. More particularly, the processing device 2702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2702 may also be one or more special-purpose processing devices such as an application specific integrated circuit (ASIC), a field programmable gate array (FPGA), a digital signal processor (DSP), network processor, or the like. The processing device 2702 is configured to execute instructions for performing any of the operations and steps discussed herein.

The computer system 2700 may further include a network interface device 2712. The computer system 2700 also may include a video display 2714 (e.g., a liquid crystal display (LCD) or a cathode ray tube (CRT)), one or more input devices 2716 (e.g., a keyboard and/or a mouse), and one or more speakers 2718 (e.g., a speaker). In one illustrative example, the video display 2714 and the input device(s) 2716 may be combined into a single component or device (e.g., an LCD touch screen).

The data storage device 2716 may include a computer-readable medium 2720 on which the instructions 2722 (e.g., implementing the application 17 or 21 executed by any device and/or component depicted in the FIGURES and described herein) embodying any one or more of the methodologies or functions described herein are stored. The instructions 2722 may also reside, completely or at least partially, within the main memory 2704 and/or within the processing device 2702 during execution thereof by the computer system 2700. As such, the main memory 2704 and the processing device 2702 also constitute computer-readable media. The instructions 2722 may further be transmitted or received over a network via the network interface device 2712.

While the computer-readable storage medium 2720 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The various aspects, embodiments, implementations or features of the described embodiments can be used separately or in any combination. The embodiments disclosed herein are modular in nature and can be used in conjunction with or coupled to other embodiments, including both statically-based and dynamically-based equipment. In addition, the embodiments disclosed herein can employ selected equipment such that they can identify individual users and auto-calibrate threshold multiple-of-body-weight targets, as well as other individualized parameters, for individual users.

The invention claimed is:

1. A method comprising:
  receiving, by a computing device associated with a control system and connected to an exercise machine via a plurality of data channels, one or more load measurements via each of the plurality of data channels, wherein the one or more load measurements are obtained from one or more load cells associated with each of the plurality of data channels and included in the exercise machine;
  in response to detecting a minimum threshold amount of load from a data channel of the plurality of data channels:
    (i) setting, by the computing device, the data channel to active, wherein the data channel set to active is associated with a first exercise included in an exercise plan,
    (ii) setting, remaining ones of the plurality of data channels to inactive,
    (iii) stopping reception of load measurements from the data channels set to inactive, wherein the data channels set to inactive are associated with exercises other than the first exercises, and
    (iv) receiving subsequent one or more load measurements via the data channel set to active;
  displaying a user interface (UI) on a display of the computing device, the displayed UI presenting information related to the subsequent one or more load measurements;
  comparing, by the computing device, the subsequent one or more load measurements to one or more respective target thresholds;

determining, by the computing device, information indicating that the subsequent one or more load measurements exceed the one or more respective target thresholds; and responsive to determining the information indicating that the subsequent one or more load measurements exceed the one or more respective target thresholds, modifying the UI to present an indication that the one or more respective target thresholds have been exceeded and the first exercise is complete.

2. The method of claim 1, wherein receiving the subsequent one or more load measurements via the data channel set to active further comprises:

receiving a left load measurement from a left load cell of the exercise machine; and receiving a right load measurement from a right load cell of the exercise machine.

3. The method of claim 2, wherein comparing the subsequent one or more load measurements to the one or more respective target thresholds further comprises: comparing the left load measurement to a left target threshold; and comparing the right load measurement to a right target threshold.

4. The method of claim 1, further comprising:

determining whether the subsequent one or more load measurements are less than the one or more respective target thresholds; and responsive to determining that the subsequent one or more load measurements are less than the one or more respective target thresholds, presenting, in the UI, an indication to recommend of applying one or more additional loads onto the one or more load cells associated with the data channel set to active to exceed the one or more respective target thresholds.

5. The method of claim 1, wherein the one or more respective target thresholds comprise an at least one osteopathic therapeutic target threshold and at least one muscular strength target threshold, and the method further comprises: determining the at least one osteopathic therapeutic target threshold based on health information pertaining to a user using the exercise machine; and determining the at least one muscular strength target threshold based on an at least one historical performance pertaining to the user previously using the exercise machine.

6. The method of claim 1, wherein the subsequent one or more load measurements comprise a left load measurement from a left load cell of the exercise machine and a right load measurement from a right load cell of the exercise machine, and the method further comprises:

presenting, in the UI, a visual representation of the left load measurement concurrently with another visual representation of the right load measurement.

7. The method of claim 1, further comprising:

responsive to determining that the first exercise in the exercise plan is complete, determining whether a second exercise in the exercise plan is incomplete;

responsive to determining that the second exercise in the exercise plan is incomplete, presenting, in the UI, an indication to begin the second exercise.

8. The method of claim 1, further comprising: responsive to determining that all exercises in the exercise plan are complete, presenting, in the UI, an indication that all exercises in the exercise plan are complete.

9. The method of claim 1, wherein a left load cell of the one or more load cells is included in a left foot platform of the exercise machine, and a right load cell of the one or more load cells is included in a right foot platform of the exercise machine.

10. The method of claim 1, wherein a left load cell of the one or more load cells is included in a left handle of the exercise machine, and a right load cell of the one or more load cells is included in a right handle of the exercise machine.

11. The method of claim 1, wherein the exercise machine is a machine enabling osteogenesis, a machine enabling muscular hypertrophy, or a combination thereof.

12. A method comprising:

receiving, by a processing device of a control system that is connected to an exercise machine via a plurality of data channels, one or more load measurements via each of the plurality of data channels, wherein the one or more load measurements are obtained from one or more load cells associated with each of the plurality of data channels and included in the exercise machine;

in response to detecting a minimum threshold amount of load from a data channel of the plurality of data channels;
  (i) setting the data channel to active, wherein the data channel set to active is associated with a first exercise included in an exercise plan,
  (ii) setting remaining ones of the plurality of data channels to inactive,
  (iii) stopping reception of load measurements from the data channels set to inactive, wherein the data channels set to inactive are associated with exercises other than the first exercise, and
  (iv) receiving subsequent one or more load measurements via the data channel set to active;

presenting, in a user interface (UI) on a display screen, one or more visual representations for the subsequent one or more load measurements;

receiving a first indication that the first exercise is complete based on the subsequent one or more load measurements having exceeded one or more respective target thresholds; and presenting, in the UI with the one or more visual representations, the first indication that the first exercise is complete.

13. The method of claim 12, further comprising:

receiving a second indication that the first exercise is within a range of being complete based on the subsequent one or more load measurements being less than the one or more respective target thresholds; and presenting, in the UI on the display screen with the one or more visual representations, the second indication that the first exercise is almost complete and to continue adding one or more loads onto the one or more load cells associated with the data channel set to active.

14. Of claim 12, further comprising:

receiving a second indication to complete a second exercise in the exercise plan based on a determination that the second exercise is incomplete; and presenting, in the UI, the second indication to complete the second exercise in the exercise plan.

15. A control system comprising:

a memory device storing instructions; and processing logic circuitry connected to an exercise machine via a plurality of data channels and operatively coupled to the memory device, wherein the processing logic circuitry is configured to execute the instructions to:

receive, via each of the plurality of data channels, one or more load measurements, wherein the one or more load measurements are obtained from one or more load cells associated with each of the plurality of data channels and included in the exercise machine;

in response to detecting a minimum threshold amount of load from a data channel of the plurality of data channels:
- (i) set flail the data channel to active, wherein the data channel set to active is associated with a first exercise included in an exercise plan,
- (ii) set remaining ones of the plurality of data channels to inactive,
- (iii) stop reception of load measurements from the data channels set to inactive, wherein the data channels set to inactive are associated with exercises other than the first exercise, and
- (iv) receive subsequent one or more load measurements from the data channel set to active;

display a user interface (UI) on a display, the displayed UI presenting information related to the subsequent one or more load measurements;

compare the subsequent one or more load measurements to one or more respective target thresholds;

determine information indicating that the subsequent one or more load measurements exceed the one or more respective target thresholds; and responsive to determining the information indicating that the subsequent one or more load measurements exceed the one or more respective target thresholds, modify the UI to present an indication that the one or more respective target thresholds have been exceeded and the first exercise is complete.

* * * * *